(12) United States Patent
Grimm et al.

(10) Patent No.: US 8,022,268 B2
(45) Date of Patent: Sep. 20, 2011

(54) TRANSGENIC ANIMAL MODEL FOR ALZHEIMER'S DISEASE

(75) Inventors: Jan Grimm, Dübendorf (CH); Roger Nitsch, Zumikon (CH); Marlen Knobloch, Zurich (CH); Uwe Konietzko, Constance (DE); Markus Rudin, Eglisau (CH); Thomas Müggler, Basel (CH); Felicitas Kranz, Zurich (CH)

(73) Assignee: The University of Zurich, Zurich (CH)

( * ) Notice: Subject to any disclaimer, the term of this patent is extended or adjusted under 35 U.S.C. 154(b) by 579 days.

(21) Appl. No.: 12/157,664

(22) Filed: Jun. 11, 2008

(65) Prior Publication Data

US 2009/0117120 A1    May 7, 2009

Related U.S. Application Data

(60) Provisional application No. 60/934,291, filed on Jun. 11, 2007.

(51) Int. Cl.
*A01K 67/027* (2006.01)
*A01K 67/00* (2006.01)
*A01K 67/033* (2006.01)

(52) U.S. Cl. .......................................... 800/18; 800/12

(58) Field of Classification Search ........................ None
See application file for complete search history.

(56) References Cited

U.S. PATENT DOCUMENTS 6,586,656 B2 *   7/2003   McLonlogue et al. ............ 800/3

OTHER PUBLICATIONS

Sigmund, C. (2000) Viewpoint: Are studies in genetically altered mice out of control? Arterioscler. Thromb. Vasc. Biology 20: 1425-1429.*
Wall, RJ (1996) Transgenic livestock: Progress and prospects for the future. Theriogenology 45: 57-68.*

* cited by examiner

*Primary Examiner* — Anne-Marie Falk
(74) *Attorney, Agent, or Firm* — John P. White; Cooper & Dunham LLP

(57) ABSTRACT

Provided is a novel APP (amyloid precursor protein) transgenic non-human animal modeling in vivo the pathophysiological effects and effects on cognitive behavior of early intraneuronal and extracellular brain parenchymal amyloid-β (Aβ) deposition and cerebral amyloid angiopathy associated with brain microhemorrhages and reduced vasoreactivity and blood flow. Furthermore, methods of screening for therapeutic or diagnostic agents useful in the treatment or diagnosis of Alzheimer's disease, in particular for improving blood flow to the brain are provided as well as the corresponding therapeutic methods.

3 Claims, 24 Drawing Sheets

D

TRANSGENIC ANIMAL MODEL FOR ALZHEIMER'S DISEASE

This application claims the benefit of U.S. Provisional Application No. 60/934,291, filed Jun. 11, 2007, the contents of which are hereby incorporated by reference into this application.

FIELD OF THE INVENTION

The present invention relates to a transgenic animal model of Alzheimer's disease and related neurological disorders. In particular, the present invention provides a transgenic non-human animal modelling the pathophysiological effects of early intra-neuronal as well as extracellular parenchymal and vascular amyloid-β (Aβ) deposits in vivo and the vascular clearance failure of Aβ. The present invention also relates to a method of producing said transgenic animal, and to methods of screening for therapeutic or diagnostic agents useful in the treatment or diagnosis of Alzheimer's disease and cerebral amyloid angiopathy. More particularly, the present invention provides a screening method for specific drugs for use in the treatment of reduced blood flow to the brain or temporary break in the blood supply to the brain due to vascular Aβ deposits in arterioles, and, less often, capillaries and veins of the central nervous system. Specifically, an animal model for validating drugs for the treatment of neurological disorders such as anti-Aβ antibodies and equivalent Aβ binding molecules for passive immunization in order to prevent the accumulation of Aβ is described.

BACKGROUND OF THE INVENTION

Generation of Aβ peptides by endoproteolytic cleavage of β-amyloid precursor protein (APP) is a central event in the pathogenesis of Alzheimers disease (AD). Several APP mutations found in early-onset familial AD (FAD) cases, including the Swedish double mutation (Swe; K670N; M671L) or various presenilin mutations, increase Aβ production or favor the production of the more amyloidogenic Aβ42 species. These aggregate to form β-amyloid fibrils in plaques and perivascular deposits, the neuropathological hallmarks of AD [34]. Transgenic (tg) expression of mutated forms of human APP or altered secretases resulting in the formation of β-amyloid plaques in mice established the functional relevance of Aβ in the pathophysiology of the disease [11, 15, 21], and initial clinical proof of concept in AD patients who generated antibodies against β-amyloid in response to vaccination underscored the relevance of β-amyloid as a target for the therapy of AD [19]. The lack of a direct correlation between β-amyloid plaque load with the severity of disease symptoms in humans and some tg mice [1, 20, 22, 33], however, suggested the possibility of smaller oligomeric Aβ aggregates as primary toxic intermediates [14, 16, 36]. Several experiments demonstrated neurotoxic effects of such intermediates in vitro and in vivo [6, 8, 10, 25, 27, 35]. Intraneuronal deposits of Aβ were also observed in brains of AD patients, in particular in brain regions affected early in AD [13], but their relation to cognitive deficits in human patients is unclear. The majority of the FAD mutations in the APP gene are close to the Aβ domain although a few point-mutations are located within the Aβ sequence at positions 692-694. Interestingly, most of these mutations, including the Arctic mutation, cause severe cerebral amyloid angiopathy (CAA) [17, 18, 23, 24, 28], possibly related to less efficient clearance of Aβ across the blood-brain barrier (BBB) [9, 18, 30]. The Arctic mutation (E693G) at position 22 of the Aβ sequence alters the aggregation properties of Aβ by accelerating the formation of protofibrils [26, 32].

SUMMARY OF THE INVENTION

The brain pathology of Alzheimer's disease is characterized by abnormally aggregated Aβ in extracellular β-amyloid plaques and along blood vessel walls, but the relation to intracellular Aβ remains unclear. To address the role of intracellular Aβ deposition in vivo, human APP with the combined Swedish and Arctic mutations were expressed in mice (arcAβ mice). Intracellular punctate deposits of Aβ occurred concomitantly with robust cognitive impairments at the age of 6 months before the onset of β-amyloid plaque formation and cerebral β-amyloid angiopathy. β-Amyloid plaques from arcAβ mice had distinct dense-core morphologies with blood vessels appearing as seeding origins, suggesting reduced clearance of Aβ across blood vessels in arcAβ mice. The co-incidence of intracellular Aβ deposits with behavioral deficits support an early role of intracellular Aβ in the pathophysiological cascade leading to β-amyloid formation and functional impairment. Furthermore, aging ArcAβ mice display microgliosis and astrocytosis as well as spontaneous brain microhemorrhages. In addition, the transgenic mice showed behavioral performance typically observed for patients suffering from a progressed stage of Alzheimer's disease such as impaired working memory. Hence, the transgenic mice of the present invention quite closely model the phenotype of humans which suffer from Alhzeimer's disease, making the animal model a useful tool for studying the disease.

More importantly, experiments performed within the scope of the present invention demonstrate that the Aβ transgenic non-human animal of the present invention is particular useful in the screening and validation of putative drugs for the treatment of Alzheimer's disease because of the various symptoms of Alzheimer's disease the animal can be tested for. Accordingly, the non-human transgenic animal of the present invention is of particular value in preclinical studies in order to minimize the risk of side effects of a putative drug during clinical trials in human.

Thus, in a first aspect the present invention relates to a transgenic non-human animal such as a rodent, more preferably murine animal and most preferably a mouse expressing at least one transgene comprising a DNA sequence encoding a heterologous Amyloid Precursor Protein (APP) comprising at least one AD (Alzheimer's disease) pathogenic mutation or a transgene affecting AD pathogenesis, wherein said transgene is operably linked to a promoter effective for expression of said gene in the brain of said animal such that it results in the deposition of amyloid-β (Aβ) in the brain parenchyma and cerebral blood vessels and is associated with reduced brain blood flow. In particular, the present invention concerns a transgenic non-human animal, which models most, if not all symptoms of Alzheimer's disease as demonstrated in the appended examples and summarized in the impact of the present invention on research in the field of Alzheimer's disease.

Furthermore, the present invention provides a means for identification of agents that interfere, delay or inhibit a reduced blood flow to the brain, in particular in Alzheimer's disease. Such agents would be of significant clinical importance for the treatment and prevention of brain damage, in particular of early stage Alzheimer's disease or prevention of its manifestation. The provision of the animal model according to the present invention can greatly shorten the time required for screening for such agents. In this context, an antibody NI-101.10 could be validated in the animal model of the present invention to be capable of normalizing vasoreactivity and blood flow via passive immunization.

More generally, the present invention relates to a method for screening, profiling and/or isolating a drug for the manufacture of a medicament for the treatment, prevention or alleviation of a neurological disorder such as Alzheimer's disease or a disease related to amyloidosis comprising:
(a) administering at lest one test compound to the transgenic animal of the present invention;
(b) determining one or more of the following parameters:
 (i) brain β-amyloid plaque load;
 (ii) brain blood flow;
 (iii) microgliosis and/or astrocytosis;
 (iv) brain microhemorrhages;
 (v) cerebral amyloid angiopathy (CAA);
 (vi) impaired working and reference memory; and
 (vii) hippocampal long-term potentiation (LTP),
wherein the observation of an improvement of the feature in the transgenic animal compared to a control is indicative for a putative drug. Naturally, a non-transgenic littermate may serve as control in order to determine whether the phenotype of the transgenic non-human animal of the present invention reverse to normal. Furthermore, a predetermined drug known to be effective in the treatment of Alzheimer's disease also in animal trials and/or a placebo may be used for control.

As will be acknowledged by the person skilled in the art, the screening method of the present invention is particular suitable for investigation of the safety of drugs and for validation of the therapeutic efficacy of agents in the treatment of Alzheimer's disease or other neurological disorders. In this context, testing a given compound in accordance with the method of the present invention preferably includes measuring blood flow and/or frequency of microhemorrhages after administration of the test compound, wherein the observation of an improved blood flow in the transgenic animal of the present invention compared to an untreated animal and the observation of an unchanged frequency of brain microhemorrhages, respectively, compared to a control is indicative for a putative safe drug. Additionally, the screening method of the present invention is suitable for the investigation of compounds or combination therapies, wherein the observation of a reduced frequency of brain microhemorrhages in the transgenic animal compared to an untreated control is indicative for a drug that can ameliorate spontaneous brain microhemorrhages or, when used in combination therapy, can ameliorate the frequency of brain microhemorrhages that are induced by the treatment of a given compound. Accordingly, the method of the present invention is particular suited for identifying and isolating a drug for the treatment of a disease associated with reduced blood flow to the brain or an instance of a temporary break in blood supply to the brain. Needless to say, that it is particular preferred that a test compound or given drug passes all features to be determined in order to qualify for a putative drug.

In a preferred embodiment of the present invention, the transgenic animal is a mouse harboring a transgene encoding amyloid precursor protein (APP) consisting of the arctic mutation (G693G) and the Swedish mutation (KM670/671NL), under the control of the prion protein promoter (PrP) named arcAβ mouse; see also the appended examples.

In a further aspect, the present invention relates to a method for treatment, prevention or alleviation of a neurological disorder, in particular of a disease associated with reduced blood flow to the brain or with an instance of a temporary break in blood supply to the brain comprising administering to a subject in need thereof a therapeutically effective amount of a compound capable of interfering with amyloid-β (Aβ) deposition, preferably wherein the compound is an anti-Aβ antibody or an antigen binding fragment thereof.

Specifically, the present invention is directed to the use of such compounds in a vaccine for immunization of a subject against impairment of blood flow and vasoreactivity due to alterations in APP expression or processing or increased production or reduced clearance of Aβ.

Further embodiments of the present invention will be apparent in the description that follows.

DETAILED DESCRIPTION OF THE INVENTION

Figure 1:
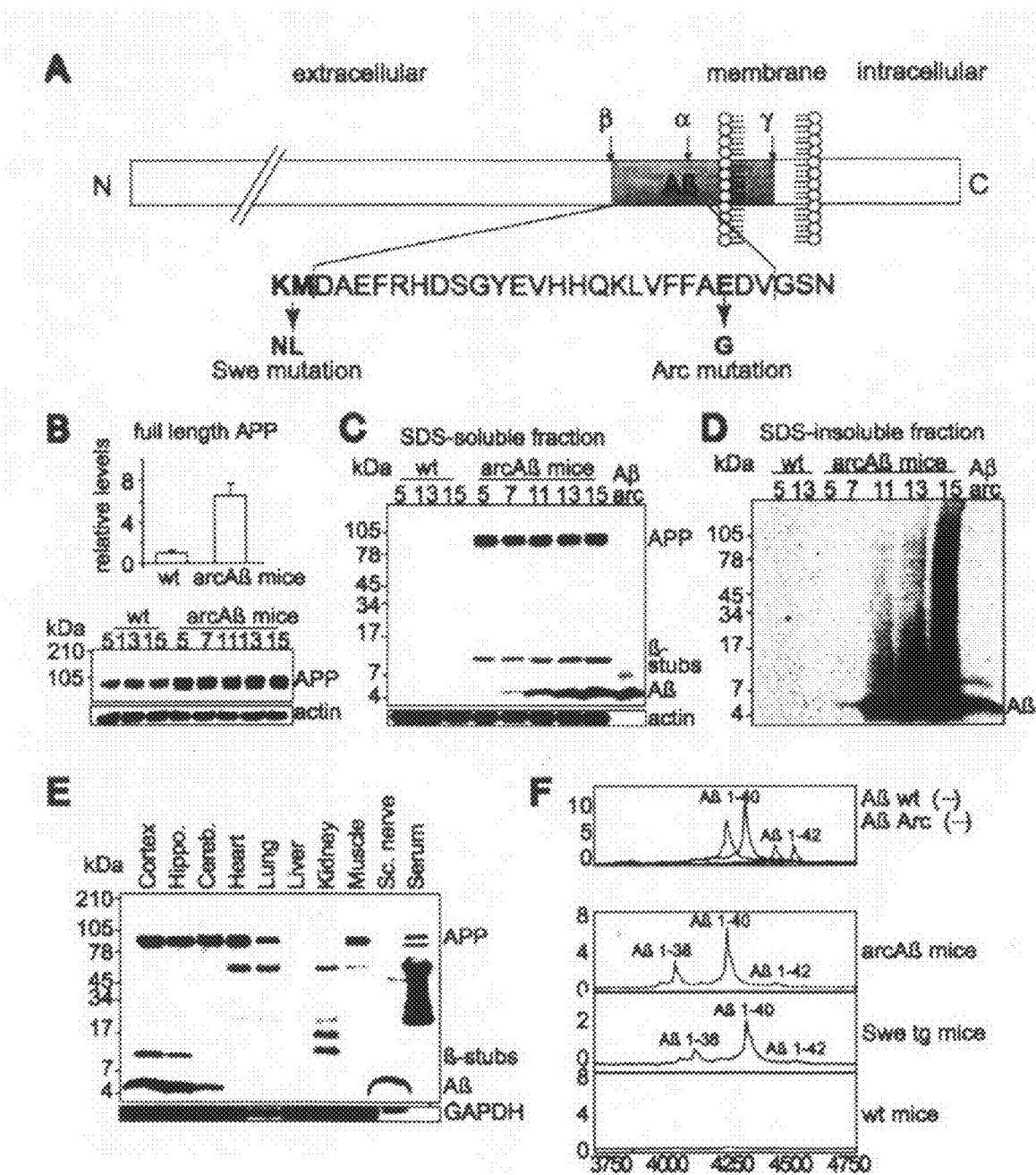
FIG. 1: (A) Schematic drawing of human APP containing the Aβ sequence and the positions of the Swe and Arc mutations. (B) ArcAβ mice with six-fold overexpression of the transgene as compared to the endogenous APP levels of wt mice, assessed by Western blotting with the Ab 22C11 against the N-terminus of APP. (C and D) Age-dependent increase in brain levels of SDS-soluble and SDS-insoluble Aβ levels without changes in levels of full length APP (n≧5 animals per age group analyzed). Representative Western blots with the Ab 6E10 that is specific for human APP, β-stubs and Aβ. (E) Presence of full-length human APP in heart, lung and muscle expressed by the Prp promoter. Aβ is only detected in nervous tissue (cortex, hippocampus, cerebellum and sciatic nerve). (F) SELDI TOF MS of synthetic Arc Aβ and wt Aβ (first panel) as well as SDS-insoluble brain homogenate fractions revealed a similar three-peak pattern in arcAβ mice and Swe tg mice. Two peaks showed the same molecular weight as the synthetic Aβ 1-40 (4329 Da) and 1-42 (4513 Da), the other peak corresponded to the mass of Aβ1-38 (4135 Da). All three peaks from arcAβ homogenate had a 72 Da shift in mass compared to Swe homogenate caused by the single amino acid exchange of the Arc mutation. No Aβ-related signals in homogenates of wt mice (last panel).

As demonstrated in the examples, the present invention provides a transgenic animal model showing rapid onset of Alzheimer's disease (AD)-like features which closely resemble the AD pathology in humans. The transgenic animals in accordance with the present invention show early accumulation of intracellular Aβ, deposition of amyloid plaques, deficits in synaptic transmission and deficits in learning and memory. In addition to the deposition of Aβ in the brain parenchyma, the transgenic non-human animal of the present invention is characterized by a prominent early onset accumulation of vascular Aβ, making this a unique model to study the vascular consequences of Aβ removal by immunotherapy and to allow screening of drugs such as anti-Aβ antibody candidates and equivalent binding molecules for related treatment efficacious compounds that do not elicit major side effects like the induction of brain microhemorrhages or screening for compounds that can ameliorate the frequency of brain microhemorrhages when administered alone or in combination therapy with a given compound. Moreover, since the transgenic mouse non-human animal model of the present invention revealed that Aβ deposition in cerebral blood vessels is associated with a reduced blood flow to the brain the present invention provides means and methods for diagnosing and preventing or ameliorating and thus normalizing impaired blood flow by applying specific drugs that can effect the vascular deposition of Aβ.

Thus, the present invention relates to a transgenic non-human animal such as a rodent, more preferably murine animal and most preferably a mouse expressing at least one transgene comprising a DNA sequence encoding a heterologous Amyloid Precursor Protein (APP) comprising at least one AD (Alzheimer's disease) pathogenic mutation or a transgene affecting AD pathogenesis, wherein said transgene is operably linked to a promoter effective for expression of said genes of the brain of said animal, which results in the deposition of amyloid-β (Aβ) in the brain parenchyma and cerebral blood vessels and is associated with reduced brain blood flow.

Methods for generating transgenic non-human animals, wherein the transgene is integrated in the genomic DNA of the animal as well as various kinds of AD pathogenic mutations are well known to the person skilled in the art; see for example international application WO2005/089539, the disclosure content of which is incorporated herein by reference, in particular with respect to the disclosure relating to AD pathogenic mutations and references cited therefore.

As described in the examples, the promoter used for expression of the mutant APP is most preferably the prion protein (PrP) promoter or a promoter with a substantially equivalent expression pattern.

In the present study, we generated a mouse-model by overexpressing human APP 695 containing both the Swedish (Swe) [31] and the Arctic (Arc) mutations under the control of the prion protein promoter (PrP) named arcAβ mouse. With combined expression of these two mutations in a single construct we hoped to achieve increased Aβ production followed by the formation of Aβ aggregates with increased stability, providing a tool to further elucidate the role of oligomeric Aβ aggregates in vivo. Surprisingly, we observed intracellular Aβ deposits that coincided with behavioral deficits before the onset of β-amyloid plaque formation and CAA.

The present invention further provides transgenic animals, preferably a mouse, which harbors at least one copy of a transgene or targeting construct of the invention, either homologously or non-homologously integrated into an endogenous chromosomal location so as to produce Arctic/Swe Aβ peptides. Such transgenic animals are usually produced by introducing the transgene or targeting construct into a fertilized egg or embryonic stem (ES) cell, typically by microinjection, electroporation, lipofection, or biolistics. Preferably, the transgenic animals according to the present invention have at least one inactivated endogenous APP allele, are preferably homozygous for inactivated APP alleles, and are substantially incapable of directing the efficient expression of endogenous (i.e., wild-type) APP.

In a preferred embodiment, a transgenic mouse is homozygous for inactivated endogenous APP alleles and substantially incapable of producing murine APP encoded by a endogenous (i.e., naturally-occurring) APP gene. Such a transgenic mouse, having inactivated endogenous APP genes, is a preferred host recipient for a transgene encoding a heterologous APP polypeptide, preferably a human Arctic mutation and the Swedish APP mutation (KM670/671NL) (APP770 numbering) to enhance both Aβ-40 and Aβ-42 Arctic peptide production. Said Swedish mutation may be replaced with similar mutations such as KM670/671DL, KM670/671DF, KM670/671DY, KM670/671EL, KM670/671EF, KM670/671EY, KM670/671NY, KM670/671NF, KM670/671KL (APP770 numbering).

However, the Swedish mutation (KM670/671NL) is presently the mutation that is most preferably combined with the Arctic mutation.

Such a transgenic non-human animal, having inactivated endogenous APP genes, is also a preferred host recipient for a transgene encoding a heterologous APP polypeptide comprising a human Arctic mutation together with a further transgene that enhances Aβ-40 and/or Aβ-42 peptide production, e.g. a further transgene encoding a heterologous presenilin-1 or presenilin-2 harboring AD pathogenic mutations. Such heterologous transgenes may be integrated by homologous recombination or gene conversion into a presenilin-1 or presenilin-2 gene locus, thereby effecting simultaneous knockout of the endogenous presenilin-1 or presenilin-2 gene (or segment thereof) and replacement with the human presenilin-1 or presenilin-2 gene (or segment thereof).

Compounds that are found to have an effect on the Aβ-Arctic peptide expression, or to promote or inhibit any of the diverse biochemical effects of Aβ Arctic peptides and/or aggregated forms of Aβ Arctic peptides such as Aβ oligomers, protofibrils, or fibrils are then further tested and used in treatment of AD and/or related neurological disorders.

In accordance with another aspect of the invention, the transgenic animal or its progeny can be used as starting points for rational drug design to provide ligands, therapeutic drugs or other types of small chemical molecules as well as proteins, antibodies or natural products. Alternatively, small molecules or other compounds as previously described and identified by the above-described screening assays can serve as "lead compounds" in rational drug design.

In particular, the non-human transgenic animal of the present invention can be characterized and tested for any one of the following parameters:
(i) brain β-amyloid plaque load;
(ii) brain blood flow;
(iii) microgliosis and/or astrocytosis;
(iv) brain microhemorrhages;
(v) cerebral amyloid angiopathy (CAA);

(vi) impaired working and reference memory; and
(vii) hippocampal long-term potentiation (LTP),
see also the appended examples.

As mentioned, the transgenic animal of the present invention is preferably characterized by the phenotype of having a reduced blood flow to the brain because of deposit of Aβ in cerebral blood vessels, which make the animal model particular suitable for drug screening. Thus, in one aspect the present invention relates to a method for screening and/or isolating a drug for the manufacture of a medicament for the treatment, prevention or alleviation of a disease associated with reduced blood flow to the brain or with an instance of a temporary break in blood supply to the brain comprising:
(a) administering at least one test compound to the transgenic animal of the present invention;
(b) measuring blood flow after administration of the test compound;
wherein the observation of an improved blood flow in the transgenic animal compared to a control is indicative for a putative drug.

As also discussed herein before, besides screening and isolating new drugs, the animal model of the present invention can also be used for validating compounds capable of interfering with Aβ accumulation or deposition for use in the treatment, prevention or evaluation of a disease associated with reduced blood flow to the brain or with an instance of a temporary break in blood supply to the brain because of Aβ deposition in the vasculature.

Hence, in a still further aspect, the present invention relates to a method for treatment, prevention or alleviation of a disease associated with reduced blood flow to the brain or with an instance of a temporary break in blood supply to the brain comprising administering to a subject in need thereof a therapeutically effective amount of a compound capable of interfering with amyloid-β (Aβ) accumulation or deposition, preferably wherein the compound is an anti-Aβ antibody or an antigen binding fragment thereof.

As described in the examples, the animal model of the present invention has been successfully employed for validating antibody NI-101.10, which besides the unique β-amyloid binding properties could also be shown to be capable of improving vasodilative properties and brain blood flow. Thus, the compound to be screened and used therapeutically is preferably an anti-Aβ antibody or an equivalent binding molecule. Anti-Aβ antibody NI-101.10, as well further anti-Aβ antibodies and Aβ binding molecules are disclosed in applicant's co-pending U.S. provisional application Ser. No. 60/878,831 "Method of providing disease-specific binding molecules and targets", filed on Jan. 5, 2007, the disclosure content of which is incorporated herein by reference. Of course, other drugs thought to be useful in the treatment of neurological disorders, in particular Alzheimer's disease can be validated in the transgenic AD animal model of the present invention as well, for example compounds can be tested as described in Klafki et al., Brain 129 (2006), 2840-2855. Epub 2006, Oct. 3; Melinkova, Therapies for Alzheimer's disease, Nat. Rev. Drug Discov. 6 (2007), 341-342; Pipeline and Commercial Insight: Alzheimer's Disease Beta Treatments on the Horizon; A Datamonitor Report, published: November 5; Product Code: DMHC212.

Thus, the present invention relates to any Aβ specific drug being capable of interfering with Aβ accumulation or Aβ related toxicity, for example by preventing the formation of and/or resolving Aβ aggregates for the treatment or immunization of a subject against impairment of blood flow due to alterations in APP expression or processing or alterations in Aβ production or clearance. Such drug is typically formulated in a pharmaceutical composition and can be administered by various routs, for example intravenously, intramuscularly, subcutaneously, intradermally, intraperitoneally, topically, intranasally, or as an aerosol.

Furthermore, the present invention relates to a polynucleotide and vector, respectively, comprising the transgene as defined hereinbefore useful in generating a transgenic non-human animal of the present invention. Preferably, the vector comprises a DNA sequence encoding a mutant APP protein comprising the Arctic mutation (E693G) and Swedish mutation (K670N; M671L) under the control of the prion protein (PrP) promoter. Most preferably, said vector is a gene targeting vector, advantageously directed to be inserted into the endogenous APP gene of the non-human animal.

The present invention also provides a pharmaceutical and diagnostic, respectively, pack or kit comprising one or more containers filled with one or more of the above described drugs, i.e., antibody or binding fragment thereof, identified and/or validated in accordance with the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, i.e. kit of the present invention is of course particularly suitable for the diagnosis, prevention and treatment of a disorder which is accompanied with the presence of a neuronal disorder-associated protein as defined above, especially amyloidosis, and in particular applicable for the treatment of Alzheimer's disease (AD).

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" or "patient" refers to a mammal, preferably a human, in need of treatment for a condition, disorder or disease.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes.

Formulations for rectal or vaginal administration may be presented as a suppository with a suitable carrier.

Furthermore, whereas the present invention includes the now standard (though fortunately infrequent) procedure of drilling a small hole in the skull to administer a drug of the present invention, in a preferred aspect, the binding molecule, especially antibody or antibody based drug of the present invention can cross the blood-brain barrier, such as antibody NI-110.10, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition. Furthermore, the pharmaceutical composition may also be formulated as a vaccine, for example, if the pharmaceutical composition of the invention comprises an anti-Aβ antibody for passive immunization.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Preferably, the therapeutic agent in the composition is present in an amount sufficient to restore normal behavior and/or cognitive properties in case of Alzheimer's disease.

The pharmaceutical compositions in accordance with the present invention can preferably be used for the treatment of neurological disorders or amyloidosis including but not limited to Alzheimer's disease, cerebral amyloid angiopathy (CAA), aphasia, Bell's Palsy, Creutzfeldt-Jakob disease, epilepsy, encephalitis, Huntington's disease, neuromuscular disorders, neuro-oncology, neuro-immunology, neuro-otology pain, pediatric neurology, phobia sleep disorders, Tourette Syndrome, Parkinson's disease, other movement disorders and disease of the central nervous system (CNS) in general.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984);

Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Supplementary Methods

Generation of Transgenic Mice

Human APP695 containing the Swe (K670N+M671L) and Arc mutations (E693G) was generated by site directed mutagenesis of pGEM-9zf(−)-huAPP695. The cDNA was inserted into pMoPrP-Xho [3], and the construct was sequenced. After removal of the vector sequence, the linear construct was injected into pronuclei of fertilized zygotes of B6D2F1 mice. Founders were screened for transgene expression by tail PCR and Western blot analysis, and the line used in this study was expanded on the hybrid background of C57B1/6 and DBA/2, to prevent the occurrence of health and breeding problems as experienced with other tg lines backcrossed to a pure background. The behavioral test groups were backcrossed once with pure C57B1/6 to consistently compare F1 generations of mice.

Behavioral Studies

Mice were kept under standard housing conditions on a reversed 12 h light: 12 h dark cycle and had free access to food and water. All mice used in the behavioral study were tested at a single timepoint (3, 6 or 9 months) in all the tests. Each test group consisted of 14-16 tg males and females and 14-16 wt littermates, balanced for gender. The experimenter was blinded during the entire testing period. Animal experiments were approved by the veterinary office of the cantonal Health Department.

Mini-Neurological Examination, Rotarod and Hotplate

The general health status of the mice was assessed with a modified battery of simple examinations [4, 7]. Mini-neurological examination: Mice were weighed and their coat appearance, the presence or absence of secretory signs and the body posture when placed in a becherglas were registered. The eye blink reflex was tested with the tip of a cotton-bud, the pupillary reflex was assessed by shining with the beam of a flashlight at the eye of the mouse. The flexion reflex was checked by pinching the hind foot of the mouse with a pair of forceps, and the ability to land on all four paws after a backflip somersault was considered as a normal righting reflex. Muscular strength was determined by pulling softly at the tail of the mouse while it was holding a grip attached to a spring balance (Newton meter).

Rotarod: To assess motor coordination mice were trained twice for 3 min to stay on a rotating rod (Udo Basile, Milano, Italy) with a constant speed of 4 rpm. Upon training, the rod was accelerated up to 40 rpm within 4 min and the latency to fall down was measured in 3 trials at the same day and once the next day.

Hotplate: Pain sensitivity was measured using a Hotplate apparatus (Medax GmbH, Germany) set to 52° C. and animals were removed after the first sign of discomfort (fore- or hindpaw-licking).

Open-Field and Zero-Maze

Both tests were conducted as described [37]. Open-field and zero-maze: In the open-field test, four mice were placed at the same time in 4 quadratic arenas (50×50 cm, 37 cm high) for 30 min. Animals were video-tracked using the Noldus EthoVision 3.00 system (Noldus Information Technology, Wageningen NL, www.noldus.com) and the time spent in the arena centre and the total distance moved were measured. For the Zero-maze test, mice were placed in one of the two opposing closed sectors of a circular, elevated runway 40 cm above the floor. They were video-tracked during 5 min and the time spent in the open area and the total distance moved was measured. Additionally, the number of head dips was recorded manually. Data from both tests were analysed using the public domain software Wintrack 2.4.

Y-Maze

The spontaneous alternation rate was assessed using a Yshaped plastic maze, with 40 cm×20 cm×10 cm arm sizes. During 5 min sessions, the sequences of arm entries were recorded; alternation was defined as successive entries into the three arms, in overlapping triplet sets. The percent alternation was calculated as the ratio of actual to possible alternations (defined as the total number of arm entries−2)×100%.

Morris Water Maze (MWM)

The MWM was conducted as described with slight modification [37]. Briefly, mice were tested in a 150 cm circular arena with opaque (Acusol™) water (25+1° C.) in a 5 day paradigm of 6 daily trials (120 s max.) with 3 days initial acquisition and 2 days with reversed platform position in the opposite quadrant. A 14 cm×14 cm goal platform was hidden at a constant location 0.5 cm below the surface, 35 cm from the wall. Various spatial cues were displayed around the pool. Mice were tracked with the Noldus EthoVision 3.00 system. Before the reversal on day 4, an additional trial without the platform was done. Data from the probe trial and the first reversal trial were pooled and analyzed for the percentage of time spent in the goal quadrant, goal zone (⅛ of pool surface) and the number of platform crossings. Video data were analyzed with Wintrack 2.4.

Two Way Active Avoidance (TWA)

Mice were tested in PC-operated two-way shuttle boxes in a 5 day paradigm (6 days for the 9 m group) with one daily 30 min session. After 2 min habituation (5 min for the first day) in the shuttle box, 80 trials with random intervals of 5-15 s were performed. Each trial started with the conditioned light stimulus alone for 5 s followed by the unconditioned stimulus (15 BA grid current) for a maximum duration of 10 s. To avoid or terminate current delivery, mice had to move into the opposite chamber. The number of correct responses, i.e. moving to the opposite chamber upon the conditioned stimulus before current delivery was analyzed.

Statistics

Data were analyzed using SAS StatView 5.0. Student's t-tests were done for comparisons of wt and tg groups. Learning performance in the MWM and TWA were analyzed by repeated measures ANOVAs.

Immunohistochemistry

Mice were anesthetized (10 ml/g bw ketamin/xylaxine) and perfused transcardially with PBS. One brain hemisphere was dissected into cortex, hippocampus and cerebellum and immediately frozen on dry-ice, the other hemisphere was fixed in 4% paraformaldehyde and embedded in paraffin. Five micrometres of sagittal sections were cut with a Leica RM 2135 microtome (Bannockburn, Ill.). Microwave pretreatement (10 min 85° C. in citrate buffer) and 5 min submersions in 95% formic acid (FA) were done before immunostaining. For DAB-stainings, sections were treated 10 min with 3% $H_2O_2$ in MeOH. After blocking of non-specific binding with 4% BSA, 5% goat serum and 5% horse serum at RT for 1 h, sections were incubated with primary Ab overnight at 4° C. at the following dilutions: 6E10 Signet) 1:400; anti-APP-CT (SIGMA) 1:200; anti-GFAβ (Adv. ImmunoChemical Inc.) 1:200; anti-Aβ3-CT (A1340 specific, SIGMA) 1:200; anti CD31 (BD Pharmingen) 1:100; Microglia Ab (gift from Prof. Imai) 1:500. For immunofluorescence, fluorophor-conjugated Abs were used for 2 h RT. DAB stainings were done with the Vectastain AβC kit (Vector LAboratories, Inc.). Congo-red and Thioflavin S stainings were done according to standard protocols. Sections were imaged by both conventional (DAB staining) and laser confocal microscopy (fluorescence staining; shown are projections of several stacks). Automated plaque counting was done with the software ImageJ (http://rsb.info.nih.gov/ij/) by using sections from 20 animals stained with 6E10/DAB (n=3 for 3m, n=7 for 5.5-7 m, n=5 for 9 m, n=5 for 15 m).

The accumulation of intraneuronal Aβ was counted by two blinded experimenter on high magnification images of the CA1/Subiculum region from arcAβ mice stained with the anti Aβ-CT Ab/DAB (2 images/mouse; n=3 for 3 m, n=5 for 7 m, n=5 for 15 m).

Protein Extracts and Western Blotting

Brain tissues were homogenized with a glass teflon homogenizer in 15 vols of buffer (100 mM Tris, 150 mM NaCl, 1% Triton, 2% SDS and protease-inhibitor). 100,000 g pellets (1 h) were resolved in 70% FA and neutralized with 10 M NaOH. Total protein concentrations were measured with the DC protein assay (BioRad Labs). Extracts were separated by SDS-PAGE, blotted onto nitrocellulose, boiled for 5 min in PBS, and blocked in TBS containing 4% milk for 1 h at RT. Primary Abs were incubated overnight at 4° C. (6E10 1:500; 22C 11 1:400) and visualized by peroxidaseconjugated Abs and ECL reactions (Amersham Biosciences).

SELDI TOF MS

PS20 arrays were coated with 0.1 mg/ml protein G (SIGMA) for 1 h, free active sites were blocked with 0.5 M ethanolamine, and 0.5 mg/ml 6E10 was coupled to the protein G and incubated with FA extracts for 2 h at RT. Synthetic Aβ 1-40 and 1-42 (Bachem) with and without the Arctic mutation was used as a positive control. 0.8 βl of 20% CHCA in 50% acetonitrile and 0.5% TFA was used as matrix to generated TOF mass spectra in a Ciphergen Biosystems System II spectrometer. Due to different ionization characteristics of Aβ 1-40 and 1-42 in SELDI, no quantitative analysis was performed.

Example 1

Age-Dependent Increase in Brain Levels of SDS-Soluble and SDS-Insoluble Aβ

ArcAβ mice (FIG. 1A) were analyzed for brain expression levels of full length human APP (hAPP), and a line with six-fold overexpression compared to the endogenous APP levels of wildtype (wt) mice was chosen for further analysis (FIG. 1B). The arcAβ mice showed constant levels of fulllength hAPP and age-dependent increases in Aβ levels, both in the 2% SDS-soluble and in SDS-insoluble fractions, (FIGS. 1C and D). Due to the known expression pattern of the PrP-promotor, the construct was not only expressed in brain, but also in extraneuronal tissues including heart, lung and muscle. Nevertheless, Aβ was detected only in brain and sciatic nerve, implying that the generation or accumulation of Aβ occurs preferentially in neuronal tissues (FIG. 1E). The absence of full-length hAPP and C-terminal stubs in sciatic nerve fibers points to a close to complete degradation of APP by combined β- and β-secretase activity. Surface enhanced laser desorption ionization time of flight mass spectrometry (SELDI TOF MS) of synthetic Arc Aβ and wt Aβ and the SDS-insoluble brain homogenate fractions revealed a similar three-peak pattern in arcAβ mice and Swe tg mice (FIG. 1F). Two peaks showed the same molecular weight as the synthetic Aβ 1-40 (4329 Da) and 1-42 (4513 Da) (FIG. 1F first panel), the other peak corresponded to the mass of Aβ31-38 (4135 Da). All three peaks from arcAβ homogenate had a 72 Da shift in mass compared to Swe homogenate caused by the single amino acid exchange of the Arc mutation.

Example 2

Intracellular Punctate Deposits of Aβ in ArcAβ Mice

Figure 2:
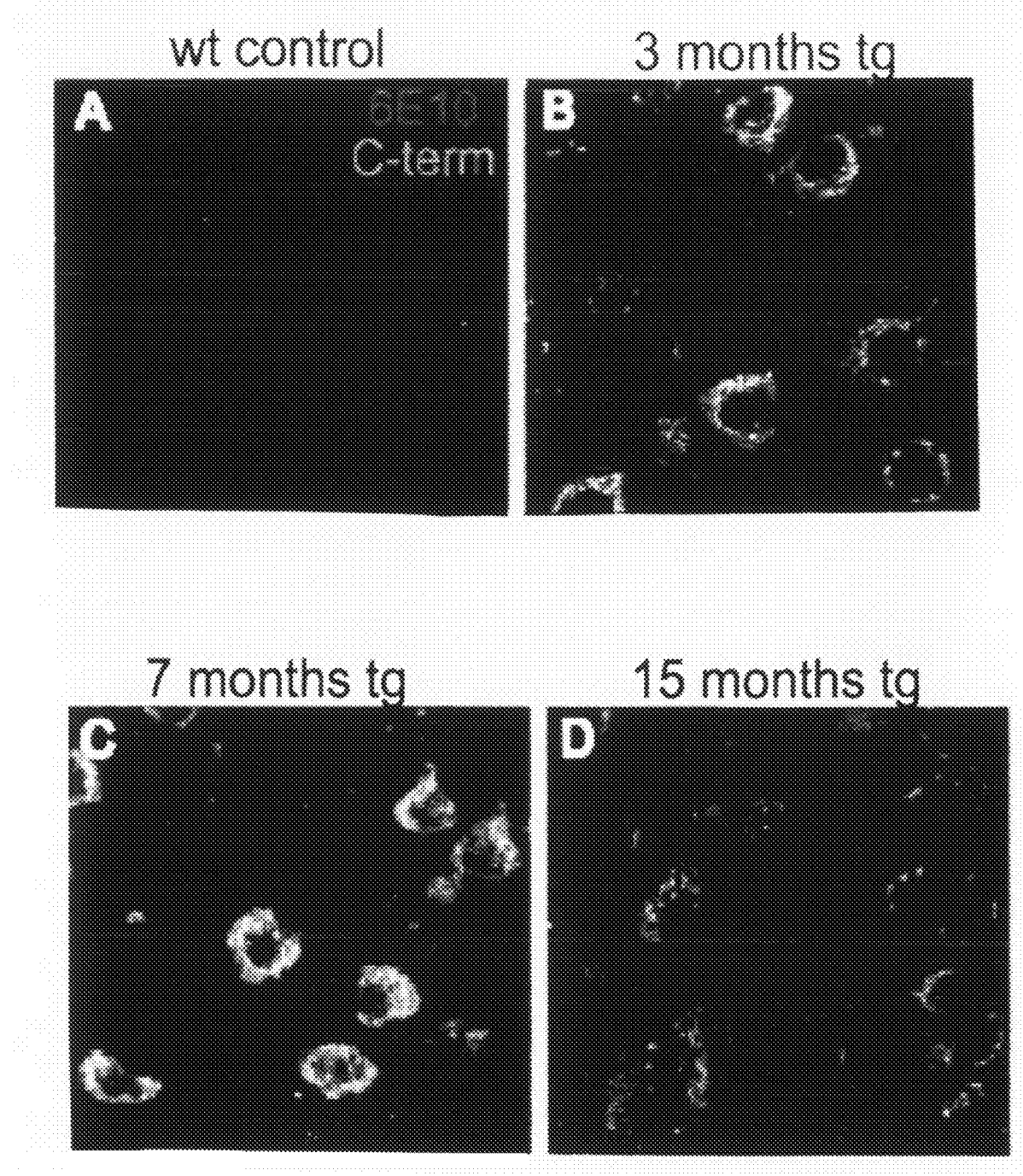
FIG. 2: Intraneuronal punctuate deposits of Aβ in arcAβ mice. (A-D) Double stainings with 6E10 (red) and anti-APP-CT (green) shows transgenic expression of full length APP in tg mice in cortex. Initial intraneuronal Aβ deposits (red) are detectable at the age of 3 months, and increase with age. (E and F) These intraneuronal structures also stain in a corresponding manner with the anti-Aβ-CT. (G) Confocal image of CA1/subiculum of a 7 months old tg mouse double stained with an ER-marker (calreticulin, in green) and 6E10 (in blue) shows the intracellular nature of the Aβ accumulation, just outside of the ER. Shown are the x-y; x-z and y-z projections. (H) Quantitative analysis of intraneuronal Aβ deposits in hippocampal CA1 and subiculum regions from tg mice (anti-Aβ-CT; 2 images/mouse; n=3 for 3 m, n=5 for 7 m, n=5 for 15 m). A significant increase of intraneuronal Aβ (p=0.02; Mann Whitney) occurred between 3 and 7 months. Scale bar 20 βm for all images.
Figure 2:
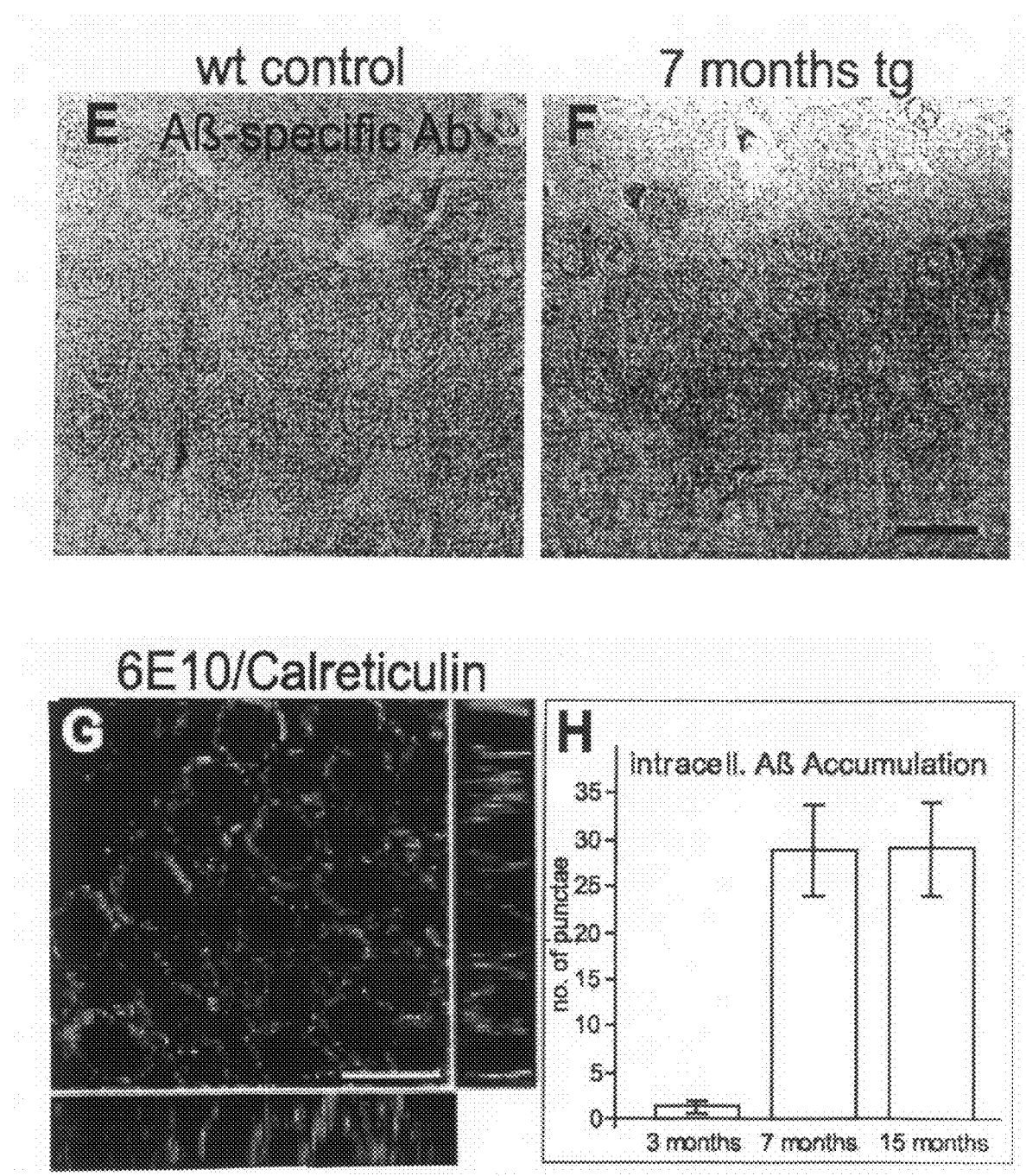

Many cortical and hippocampal neurons in arcAβ mice were positively labeled with 6E10 (red), and with anti-APPCT against the C-terminus of APP (green). As expected, anti-APP-CT co-stained full length APP and β-stubs in many 6E10-positive neurons. In addition, 6E10 detected numerous intracellular punctate Aβ deposits that were not seen with anti-APP-CT (FIG. 2A-D). These were labeled with anti-Aβ-CT, a selective antibody against the C-terminus of Aβ, confirming that they consisted of the complete Aβ sequence (FIGS. 2E and F). Confocal analysis with the ER-marker calreticulin (green) established that the intracellular Aβ deposits (blue) accumulated outside of the ER (FIG. 2G). Intracellular Aβ deposits occurred already at 3 months of age (FIG. 2B), and their amounts increased significantly with aging (p=0.02) to attain a maximum between 7 and 15 months (FIGS. 2C, D and H).

Example 3

Age-Dependent Cognitive Impairment in ArcAβ Mice

Figure 3:
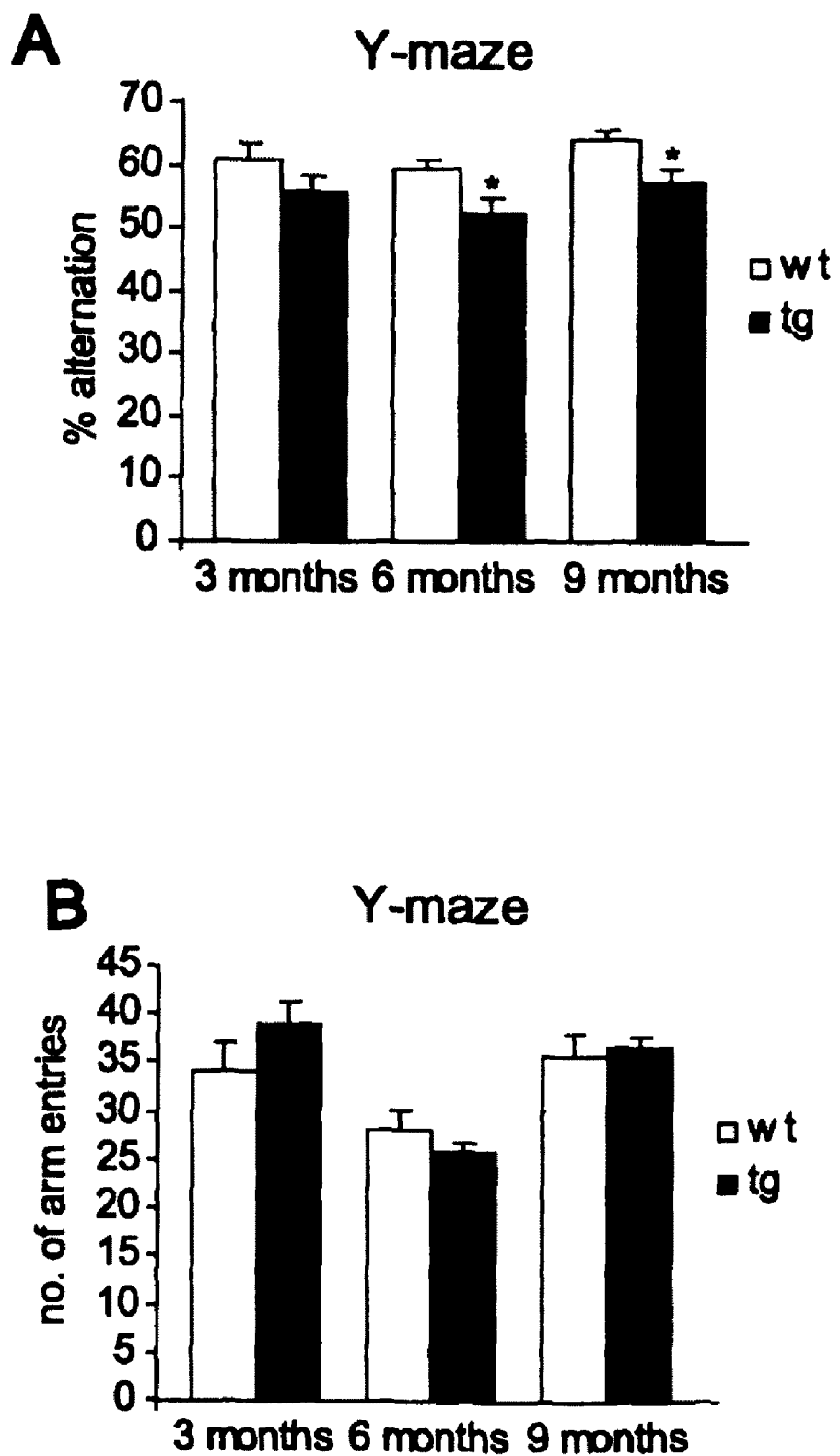
FIG. 3: Cognitive impairments at 6 months of age. (A) A cross-sectional behavioral study with different age groups showed an impairment of arcAβ mice compared to age matched littermates at 6 months (p=0.02) and 9 months of age (p=0.01) in the Y-maze, a primitive working memory test measuring spontaneous alternation behavior. (B) The reduced alternation levels were not caused by a general lack of explorative activity indicated by unchanged total numbers of arm entries between tg and wt mice. (C-E) No significant differences in escape latencies in the MWM during the acquisition and reversed learning phases in any age group. (G and H) In contrast, in the probe trials 6- and 9 month-old arcAβ mice spent significantly less time in the goal quadrant and crossed the position of the learned platform less often than their wt littermates (p=0.02 for goal quadrant, p=0.02 for no of platform crossings for 6 months; p=0.009 for goal quadrant, p=0.05 for no of platform crossings for 9 months). (F) No difference in memory retrieval in 3 month-old arcAβ mice. (J and K) The cognitive impairment was also evident in the TWA, a Pavlovian conditioning learning paradigm, where arcAβ mice at 6 months (p<0.0001 for interaction correct response×genotype, p=0.0002 for last day) and 9 months of age (p=0.0004 for interaction correct response×genotype, p=0.04 for last day) performed significantly less well than their wt littermates. (I) No significant impairment in 3 month-old arcAβ mice. Values are means±S.E.M., n=14-16 mice per group, Student's t-tests and repeated measurement ANOVAs were used for statistical analysis
Figure 3:
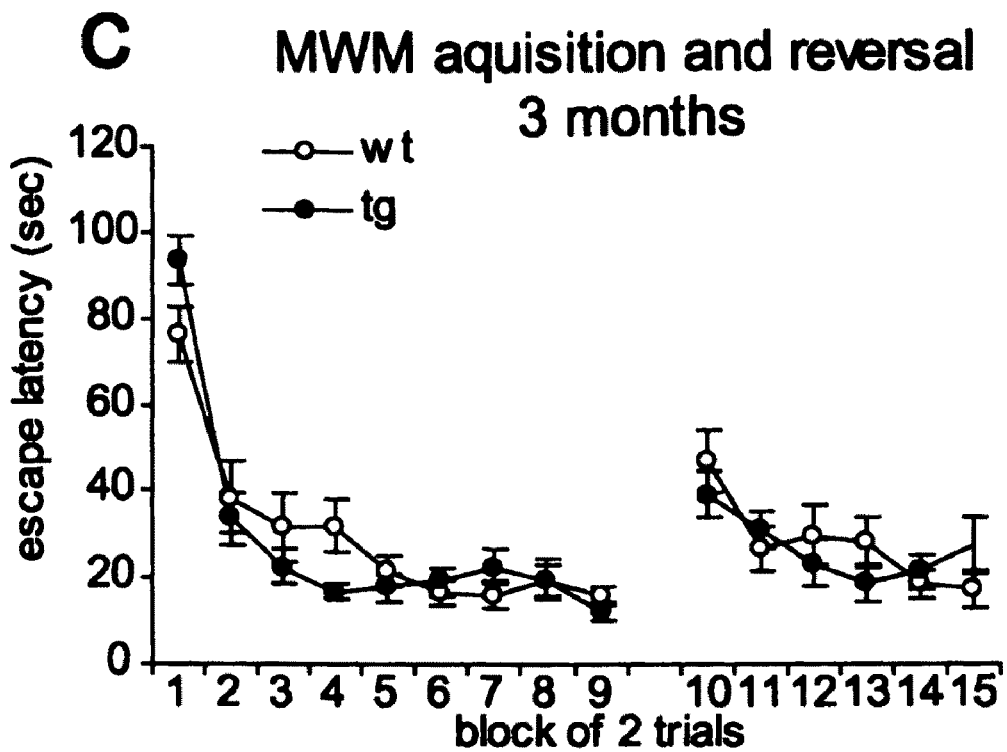
Figure 3:
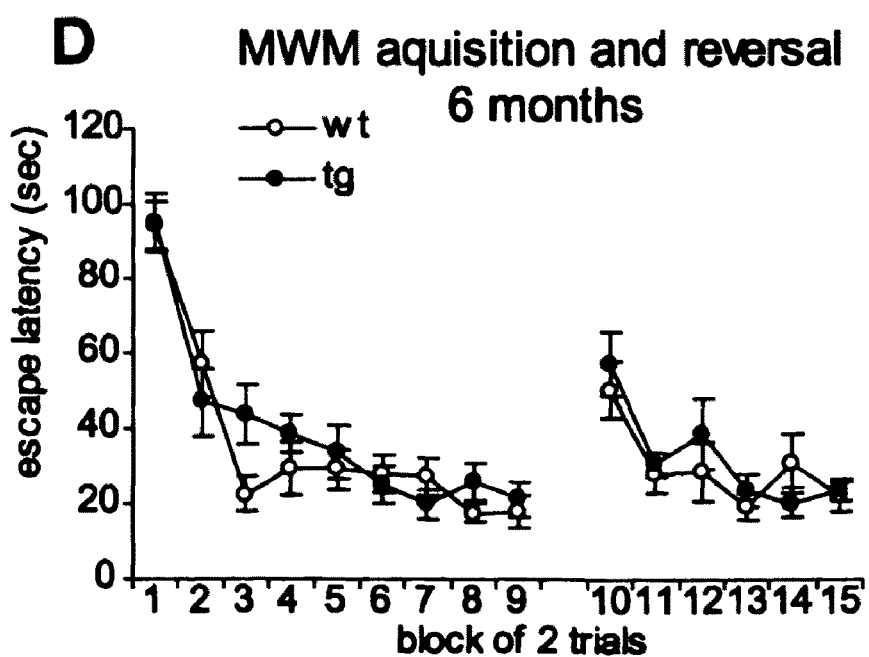
Figure 3:
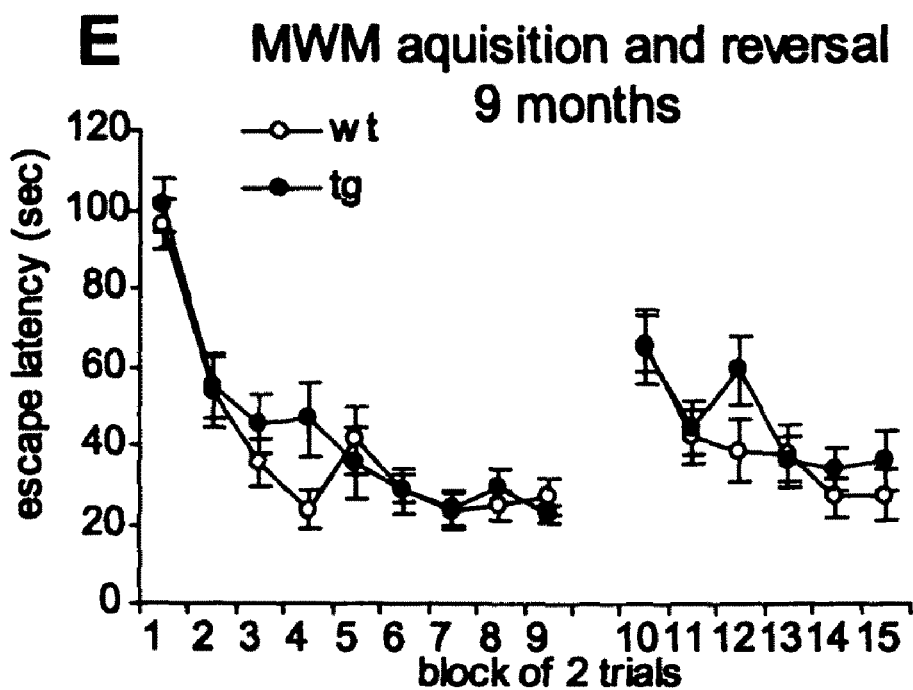
Figure 3:
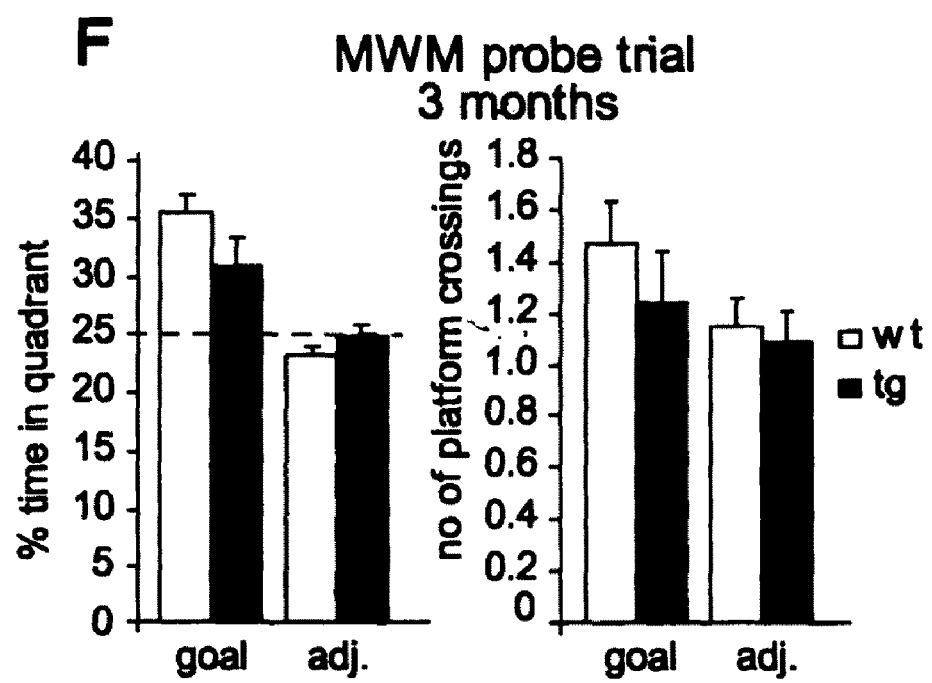
Figure 3:
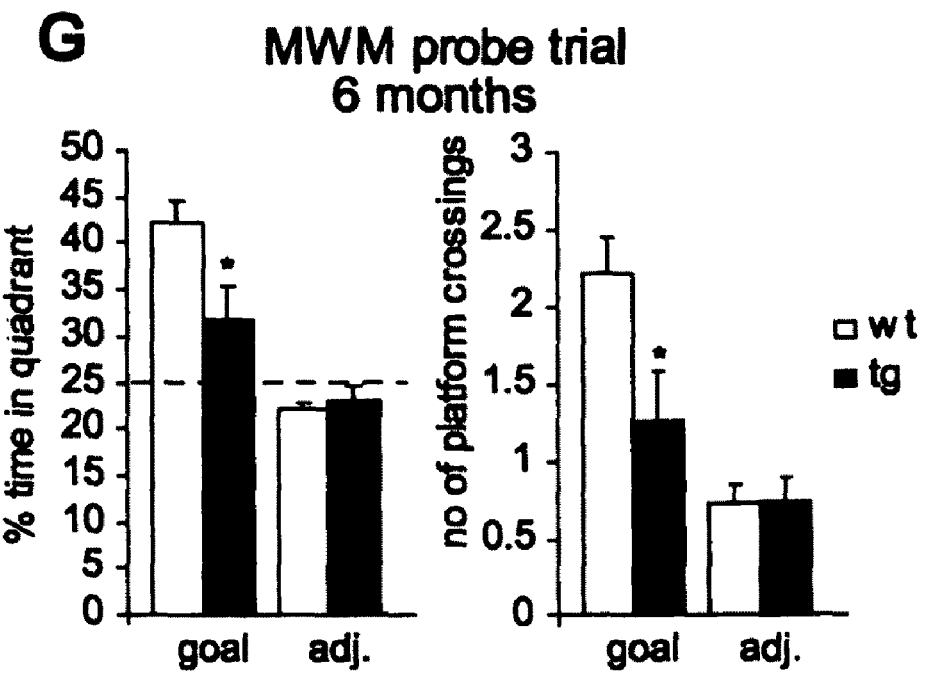
Figure 3:
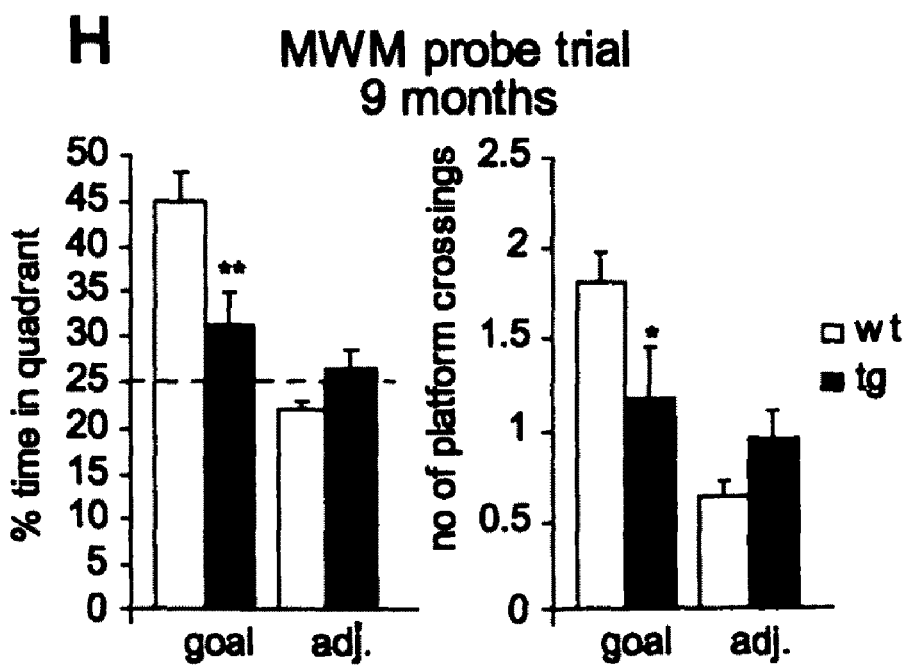
Figure 3:
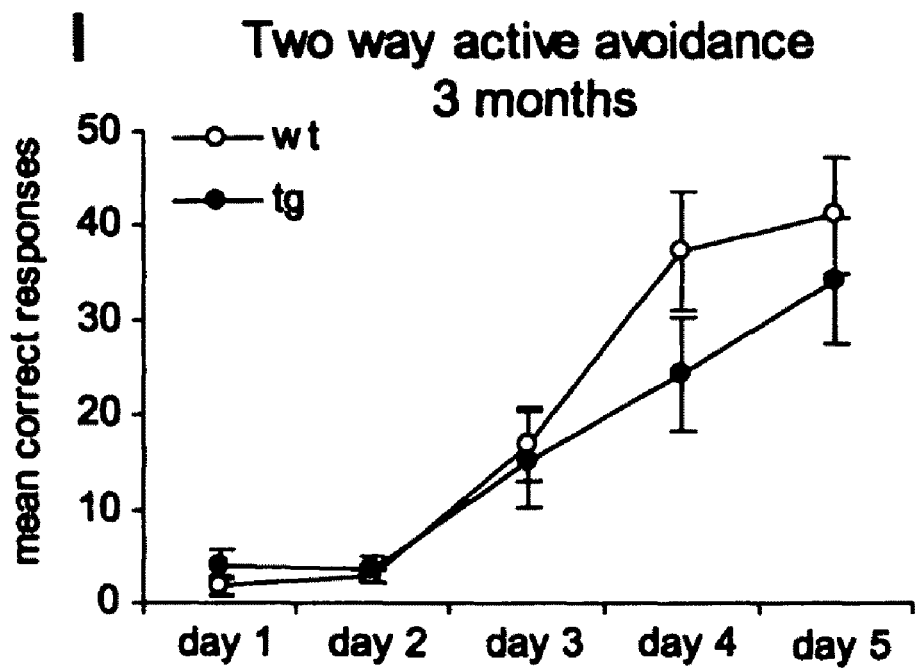
Figure 3:
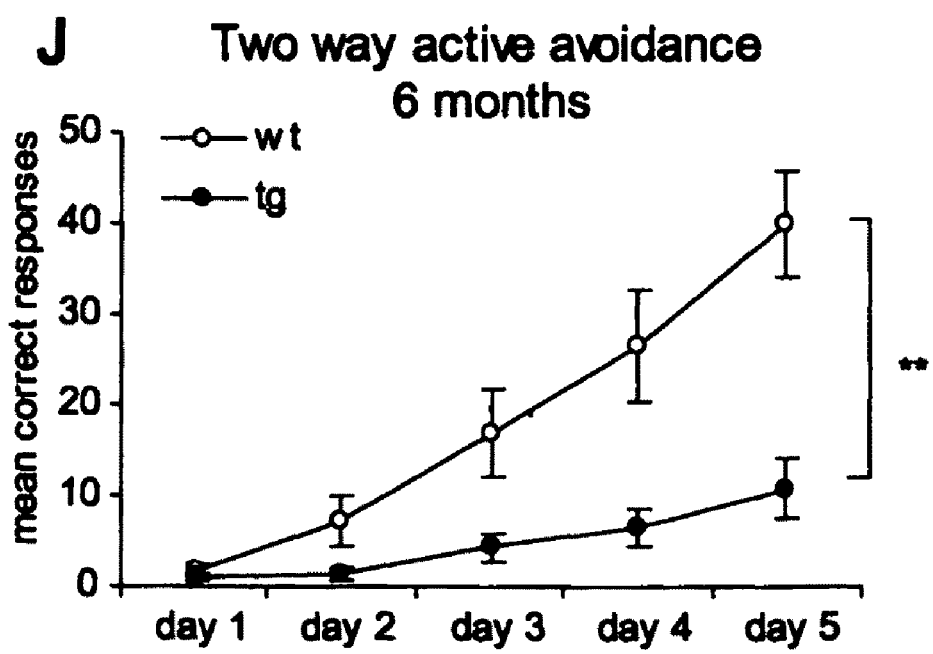
Figure 3:
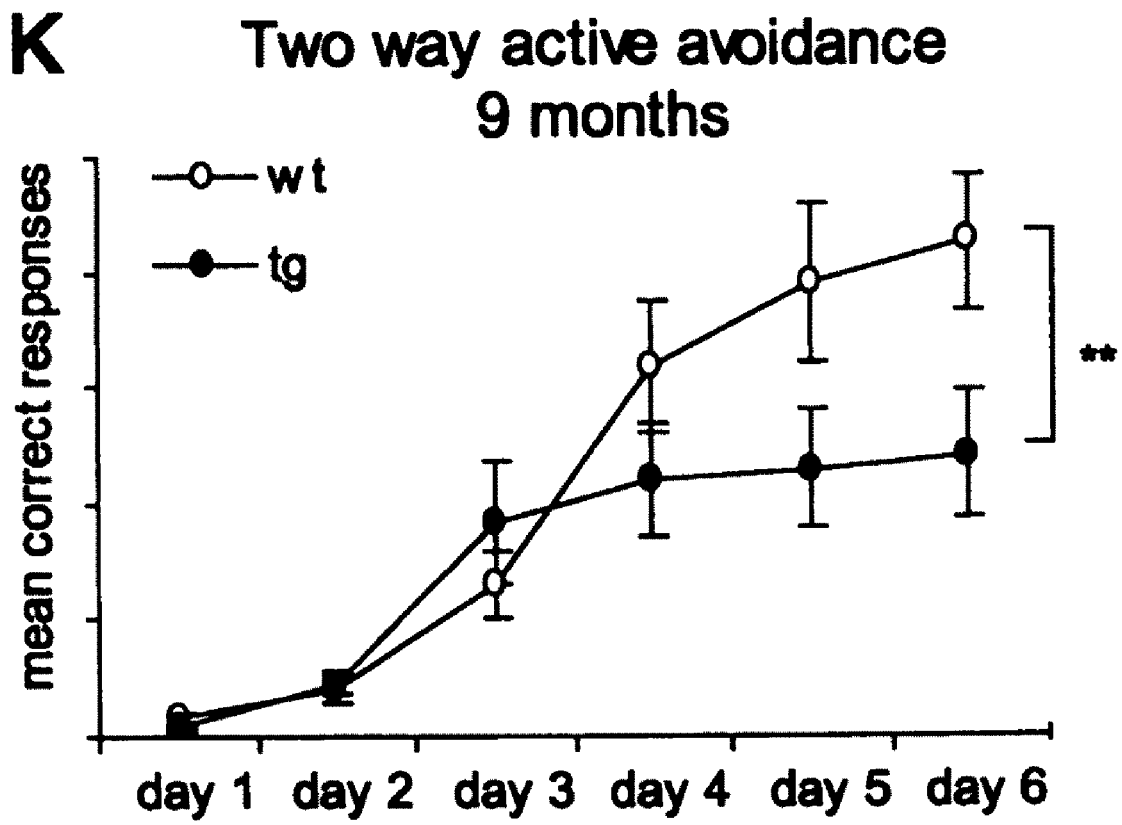
Figure 4:
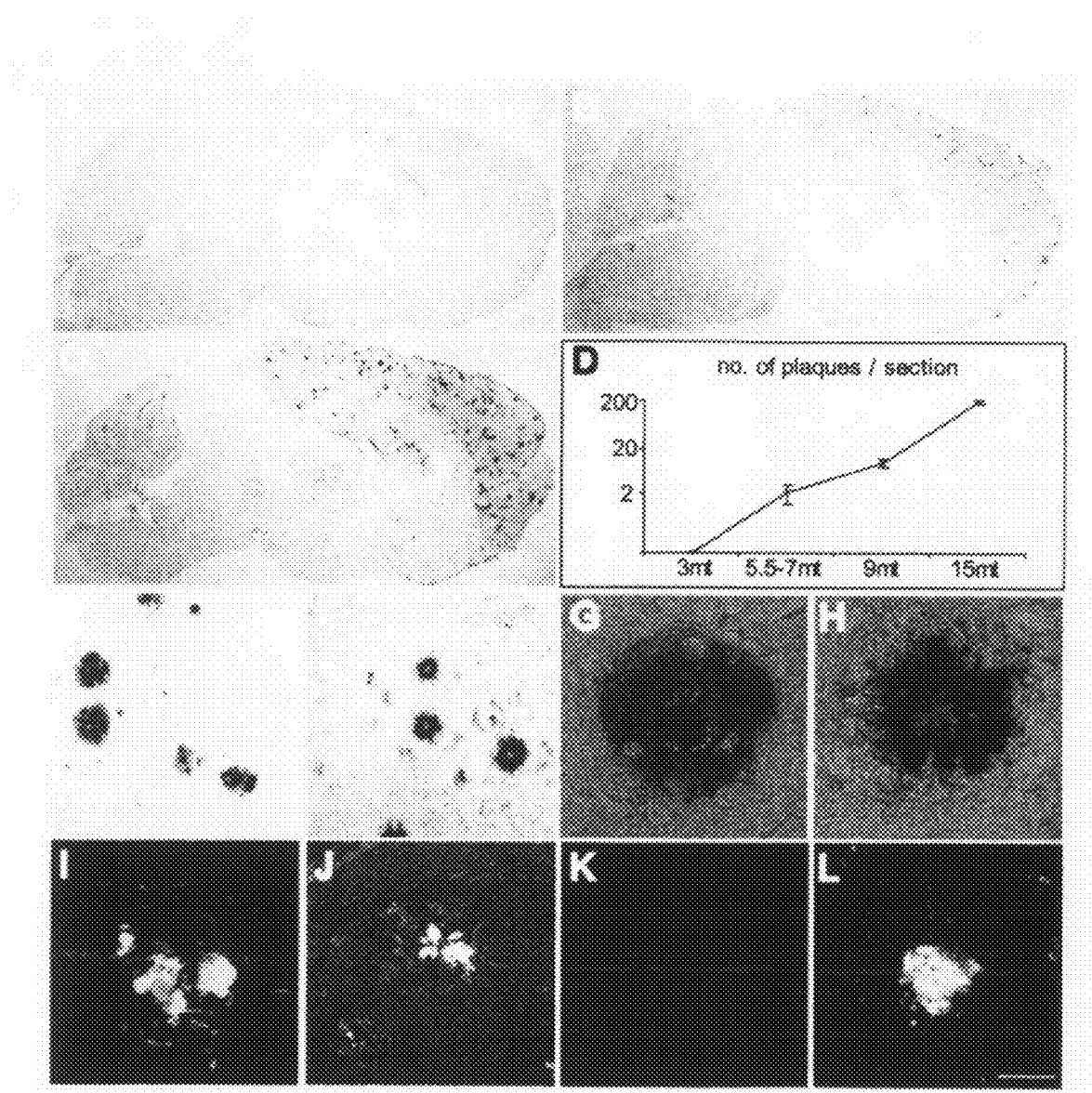
FIG. 4: The Arc mutation causes distinct dense core β-amyloid plaque morphology. Initial β-amyloid plaques appeared after 7 months of age followed by consistent and rapid increases in numbers between 9 and 15 months. Overview images showing β-amyloid plaque pathology of arcAβ mice at: (A) 7 months, (B) 11 months and (C) 15 months of age (D) increase in β-amyloid plaques (n=3 for 3 months, n=7 for 5.5-7 months, n=5 for 9 months, n=5 for 15 months). (E and G) β-Amyloid plaques in arcAβ mice had a distinct morphology with intensely stained cores. (I and J) By contrast, typical plaques from Swe tg mice analyzed in parallel had a cotton wool-like appearance with no densely stained cores, also seen with Thioflavin S and Congo Red (data not shown) The prominent core structure of arcAβ plaques is Thioflavin S positive and shows apple green birefringence with Congo-red staining. (K and L) Double staining with an anti-GFAβ Ab (blue) and 6E10 (red) shows reactive astrocytes around plaques as well as reactive microglia (red, 6E10 in green). Scale bar: 0.25 cm for A-C; 250 βm for E and F; 40 βm for G-L

To determine the effects on intracellular Aβ on behavior, we tested the arcAβ mice in a battery of tests covering cognitive functions and basic neurological functions, and compared them to their wt littermates. Whereas 3 monthold tg mice did not differ in cognitive performance from wt littermates (FIGS. 3A, C, F and I), 6 month-old and 9 month-old mice had impaired cognitive functions in all three paradigms tested; the Y-maze, the MWM and the TWA. In the Y-maze, the percentage of alternations was reduced (p<0.02), indicating impaired working memory (FIG. 3A). Reduced alternation behavior was not due to lack of exploration because the platform position during the acquisition and the reversal the total number of arm entries were identical between groups training in all three age classes (FIG. 3C-E). The swim speed (FIG. 3B). Similarly, in the probe trial of the MWM, tg mice (although slightly increased in the 3 months old tg mice), spent less time (p=0.02 for 6 months; p=0.009 for 9 months) did not differ significantly between wt and tg mice in all in the Nine month-old arcAβ mice were also impaired but the difference became evident only after 4 days of training. Therefore, to confirm this observation, we tested the 9 months group on an additional trial on day 6 (FIG. 3K; repeated measure ANOVA; p=0.0004; Student's t-test for last day p=0.04).

Example 4

Normal Basic Neurological Functions in ArcAβ Mice Except for Increased Sensitivity to Heat To confirm that the cognitive deficits seen were not due to general neurological impairments caused by the expression of the transgene, all mice were given a "minineurological" examination; it revealed no differences in basic health between tg and wt mice (Table 1).

TABLE 1

Mini-neurological examination

| Test | 3 month (normal/total) wt | 3 month (normal/total) tg | 6 month (normal/total) wt | 6 month (normal/total) tg | 9 month (normal/total) wt | 9 month (normal/total) tg |
|---|---|---|---|---|---|---|
| Coat appearance | 15/15 | 15/15 | 15/15 | 14/14 | 16/16 | 14/14 |
| Secretory signs | 15/15 | 15/15 | 15/15 | 14/14 | 16/16 | 14/14 |
| Body posture | 15/15 | 15/15 | 15/15 | 14/14 | 16/16 | 14/14 |
| Eye blink reflex | 15/15 | 15/15 | 15/15 | 14/14 | 16/16 | 14/14 |
| Pupillary reflex | 15/15 | 15/15 | 15/15 | 14/14 | 16/16 | 14/14 |
| Flexion reflex | 15/15 | 15/15 | 15/15 | 14/14 | 16/16 | 14/14 |
| Righting reflex | 15/15 | 15/15 | 15/15 | 14/14 | 16/16 | 14/14 |

| | 3 month (mean ± s.e.) wt | 3 month (mean ± s.e.) tg | 6 month (mean ± s.e.) wt | 6 month (mean ± s.e.) tg | 9 month (mean ± s.e.) wt | 9 month (mean ± s.e.) tg |
|---|---|---|---|---|---|---|
| Grip strength (Nm) | 76.89 ± 3.23 | 81.67 ± 3.12[1] | 95.78 ± 3.57 | 100.47 ± 2.61[2] | 93.96 ± 2.86 | 104.05 ± 4.50[3] |
| Weight (g) | 27.38 ± 1.39 | 26.65 ± 1.61[4] | 29.96 ± 1.40 | 28.86 ± 2.11[5] | 33.36 ± 1.93 | 31.61 ± 2.06[6] |
| Average time on rotarod (sec) | 190 ± 15 | 183 ± 15[7] | 157 ± 10 | 180 ± 17[8] | 144 ± 17 | 147 ± 21[9] |

[1] p = 0.29,
[2] p = 0.30,
[3] p = 0.06,
[4] p = 0.74,
[5] p = 0.66,
[6] p = 0.54,
[7] p = 0.72,
[8] p = 0.25,
[9] p = 0.90

Table 1. Mini-neurological examination. All animals of the three age groups had normal coat appearances, no secretory signs, normal body postures and normal basic reflexes, including the eye blink, pupillary, flexion- and righting reflexes. Both wt and tg mice had age appropriate body weights and no differences in muscular strength (grip strength) measured with a spring scale. No differences in motor coordination on the rotarod were found.

goal quadrant (FIGS. 3G and H left panel), and in the three age classes (data not shown). Together, these data indigoal zone (data not shown) and they crossed the correct plat-cate impaired memory retention in the absence of learning form position fewer times (p=0.02 for 6 months; p=0.05 deficits for 9 months) as compared to wt mice (FIGS. 3G and H right Six month-old arcAβ mice were highly impaired panel). Despite the clear difference in performance between (p<0.0001), however, in the TWA paradigm where a light wt and tg mice in the probe trial both groups were able to learn stimulus has to be associated with a noxious foot-shock (FIG. 3I-K). We found these deficits by repeated measurement ANOVAs (FIG. 3J; interaction number of correct responses and genotype) as well as by analyzing the performance of the last training days separately (FIG. 3J; Student's t-test for last day; p=0.0002).

Figure 6:
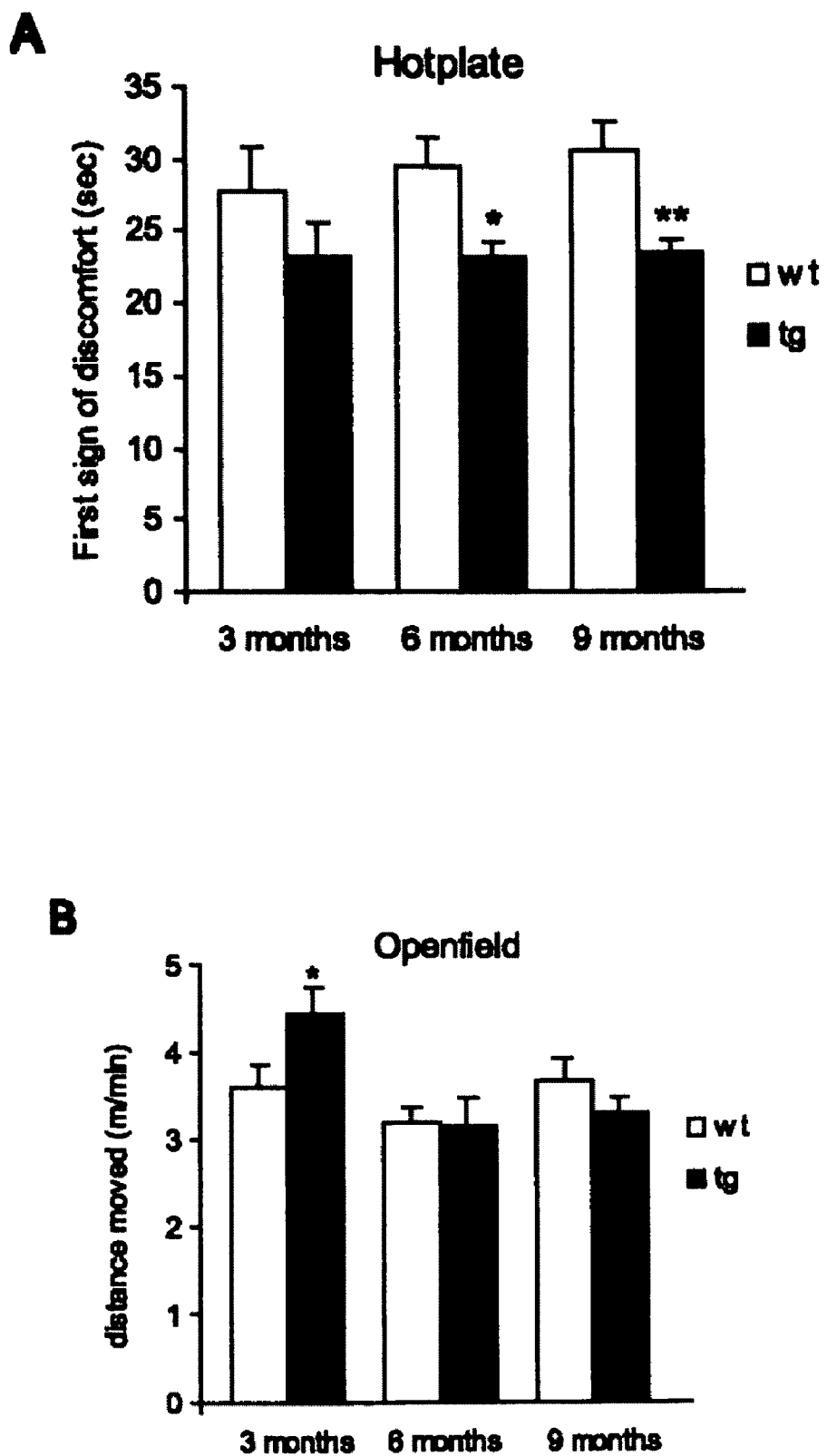
FIG. 6: Increased heat sensitivity, early locomotor and exploratory hyperactivity and increased anxiety with age. (A) The hotplate test revealed increased sensitivities of arcAβ mice to heat (p=0.01 for 6 months; p=0.007 for 9 months). (B-D) The hyperactivity at 3 month seen in the open field and zero maze (p=0.04 for distance moved and p=0.0008 for % time in center in the open field, p=0.01 for distance moved in the zeromaze) disappeared with age. (E-F) 6 and 9 months old arcAβ mice spent a significantly reduced percentage of time in the open sectors of the Zeromaze (p=0.007 for 6 months; p=0.009 for 9 months) and showed a clearly reduced amount of unprotected head dips (p=0.02 for 6 months, p=0.005 for 9 months); both measures are indicators for anxiety levels. Values are means±s.e.m., n=14-16 µg and 14-16 wt mice per age group, the Student's t-test was used for statistical analysis.
Figure 6:
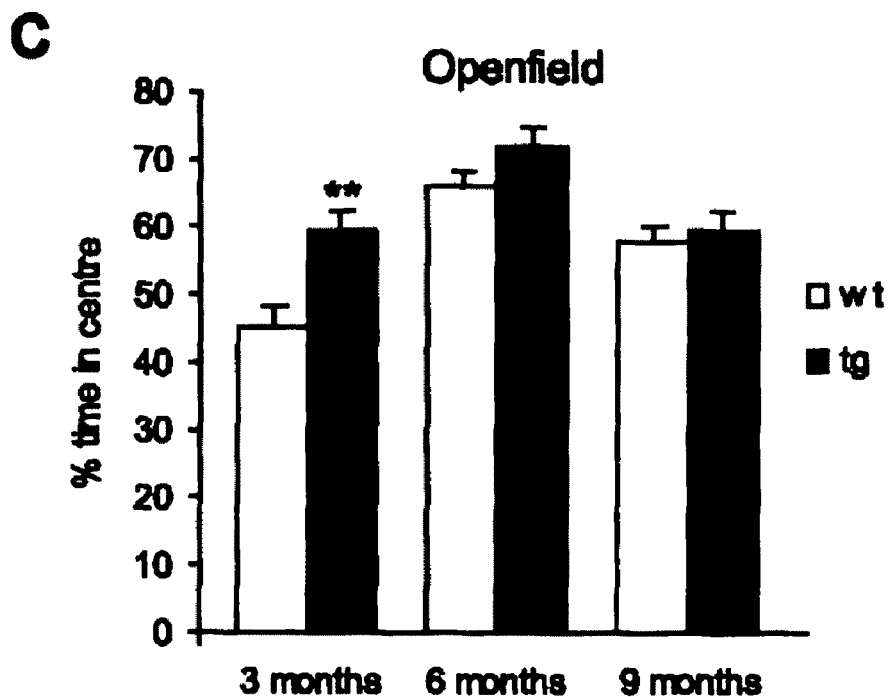
Figure 6:
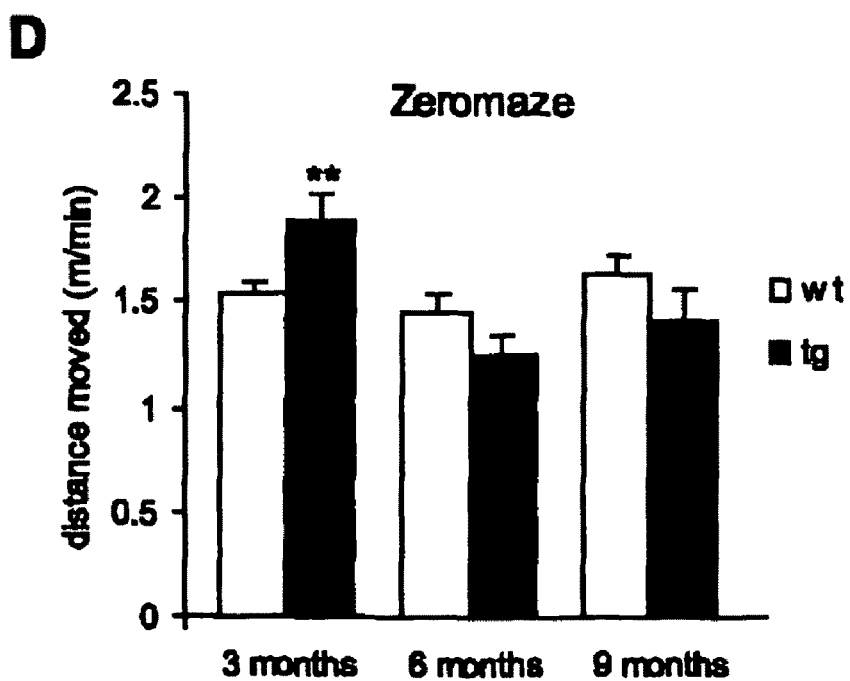
Figure 6:
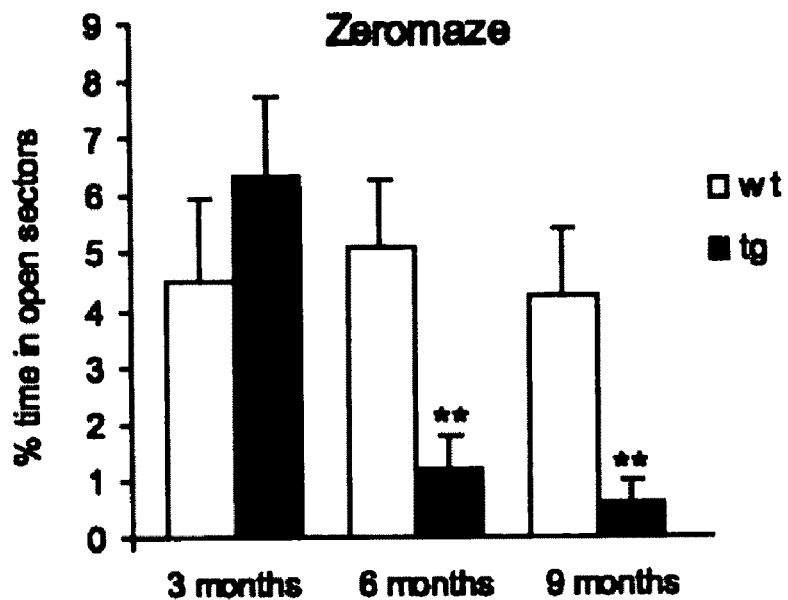
Figure 6:
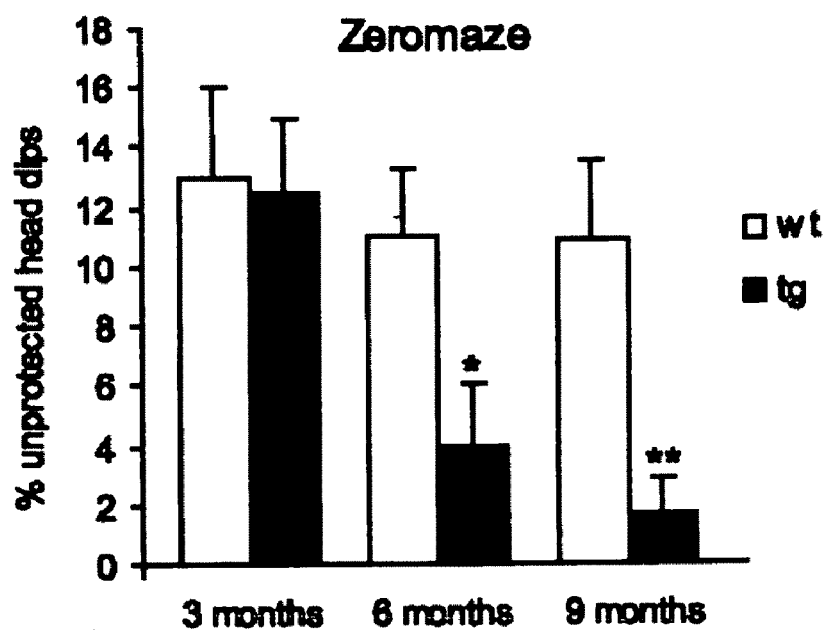

However, arcAβ mice had increased sensitivity to heat as compared to their wt littermates in the hotplate test, indicated by earlier signs of discomfort including paw licking (FIG. 6A; supporting information).

Example 5

Age-Dependent Decrease in Locomotor and Exploratory Hyperactivity Followed by Increased Anxiety Further behavioral examinations revealed a significant locomotor and exploratory hyperactivity of arcAβ mice at 3 months in the openfield and the zeromaze (FIG. 6B-E; supporting information). This hyperactivity disappeared with increasing age; at 6 and 9 months there were no more differences in locomotor activity between tg and wt mice. The exploratory hyperactivity in the zeromaze not only disappeared with age but even changed to the contrary in 6 and 9 month-old tg mice; they spent less time in the open sectors (FIG. 6E; supporting information) and showed reduced numbers of unprotected head dips (FIG. 6F; supporting information), suggesting increasing levels of anxiety with increasing age in tg mice.

Example 6

The Arctic Mutation Causes Distinct Dense Core β-Amyloid Plaque Morphology

Figure 5:
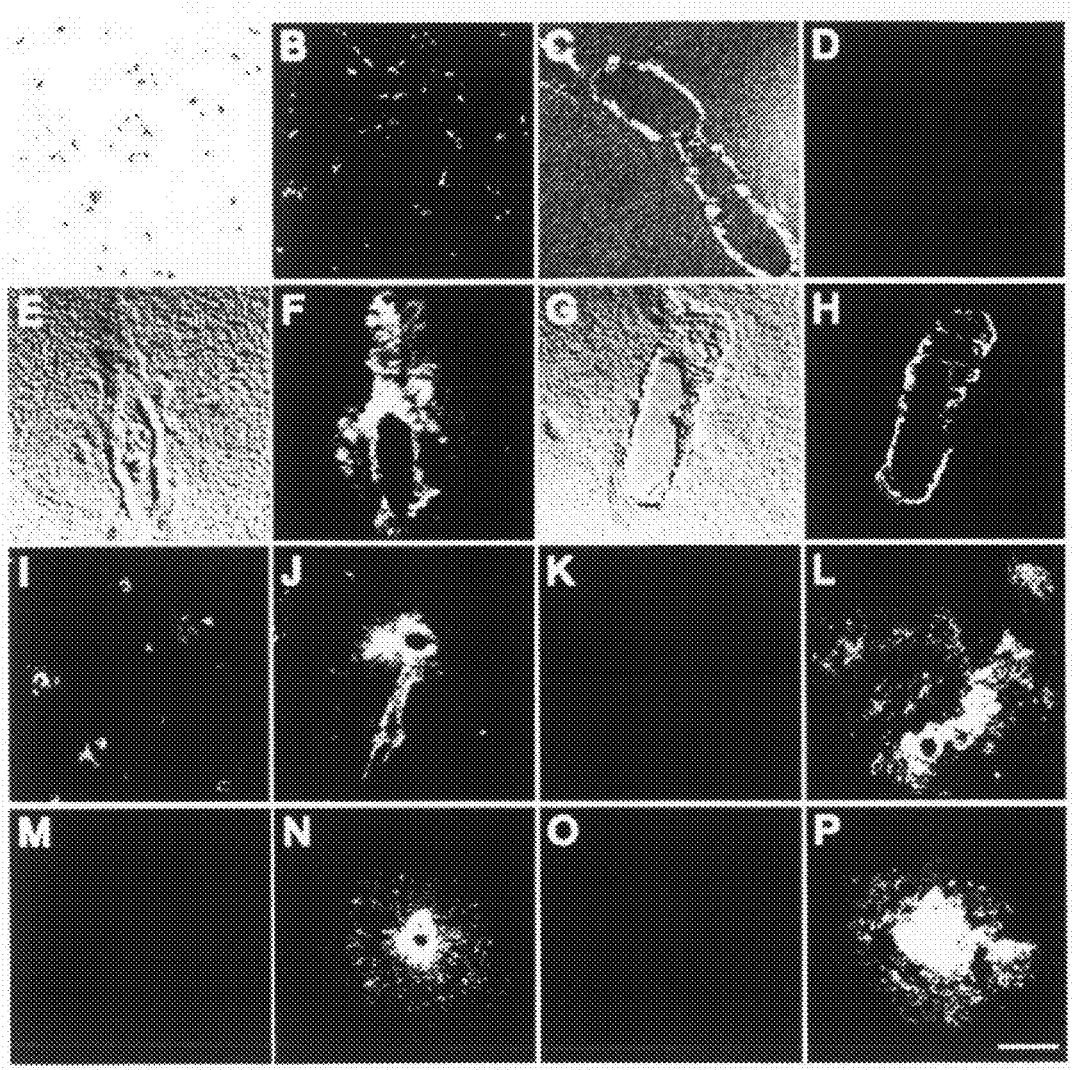
FIG. 5: Congophilic β-amyloid angiopathy; (A) CAA in arcAβ mice at 15 months stained with 6E10. (B) Thioflavin S positive β-amyloid deposits along blood vessel walls. (C) Apple-green birefringence of Congo-red staining along blood vessels. (D) Double staining with an anti-GFAβ Ab (blue) and 6E10 (red) shows reactive astrocytes around blood vessels. (E-H) The Aβ aggregates from arcAβ mice were not restricted to the vessel walls as is the case for CAA in Swe tg mice but rather spread from the walls into the adjacent brain parenchyma. (E and F) Blood vessels from arcAβ mice. (G and H) Blood vessels from Swe tg mice (confocal images of Thioflavin S staining and phase contrast images). (I and J) Blood vessels as possible seeding origins for dense cored plaques. Dense cored plaque-like deposits in arcAβ mice with a small hole in the middle of the core and blood vessels with great similarity to these plaques. (K-P) Different stages of β-amyloid deposits around blood vessels. Double staining with an Ab against CD31 (in red), a marker for blood vessel endothelium and 6E10 (in green), shown alone and in an overlay. (M and N) The hole in the middle of an arcAβ dense core plaque corresponded to the lumen of a blood vessel. (O and P) In plaques with closed cores, blood vessels surrounded the cores. Scale bars: 500 βm for A and B; 125 βm for I; 40 βm for C and D; 20 βm for E-H

Histological examination of brains from arcAβ mice revealed an age-dependent increase in β-amyloid plaque deposition, starting around 7 months, when a few animals showed initial Aβ deposits followed by dramatic increases increase was consistently found in all tg mice examined (FIG. 4A-D). The plaques from arcAβ mice were characterized by distinct morphology with intensely stained cores surrounded by less dense material (FIGS. 4E and G). By contrast, typical plaques from Swe tg mice analyzed in parallel had a cotton woollike appearance with no densely stained cores (FIGS. 4F and H), also seen with Thioflavin S and Congo Red (data not shown). Plaques from arcAβ mice were Thioflavin S positive (FIG. 4I) and Congo-red stainings of the dense cores (FIGS. 5G and H). They were not confined to the borders showed the characteristic apple-green birefringence (FIG. 4J). of vessel walls but spread from the walls over long dis—They were surrounded by reactive astrocytes (in blue) and tances into the adjacent brain parenchyma. In many cases, microglia (in red), as indicated by double labelling with Abs the arcAβ dense-cored plaques had a small hole in the cenagainst GFAβ and Iba-1 (FIGS. 4K and L).

Example 7

Congophilic β-Amyloid Angiopathy

The development of dense core β-amyloid plaques in Ab against the endothelial blood vessel epitope CD31 (red) arcAβ mice coincided with severe CAA (FIG. 5A). Thioflavin and 6E10 (green). Confocal images of these double-labels S and Congo-red positive material was deposited along blood confirmed the very close association of blood vessels with vessel walls (FIGS. 5B and C), and was accompanied by astro-Aβ deposits. These data strongly suggest that the center cytosis (FIG. 5D). These arcAβ vascular β-amyloid deposits represented blood vessels lumina (FIGS. 5K and M; L and (FIGS. 5E and F) differed from those seen in Swe tg mice N: corresponding overlays). In contrast, arcAβ dense cored plaques without a central vessel were surrounded by blood vessels (FIGS. 5O and P).

Discussion

Here we describe the phenotype of tg mice overexpressing human APP with the combined Swe and Arc mutations in a single construct (arcAβ mice). The arcAβ mice were cognitively impaired from the age of 6 months on in MWM and Y-maze as well as in active avoidance behavior. At this age, intracellular punctuate deposits of Aβ were abundant in cortex and hippocampus with no apparent β-amyloid plaque load. This co-incidence of cognitive deficits with intracellular Aβ deposits suggests the possibility that they contributed to the behavioral deficits and further supports the hypotheses that intracellular Aβ impairs neuronal functions [36]. The presence of intracellular Aβ deposits in our ArcAβ mice could be related to the chemical properties of the Arc Aβ oligomers, that may be more stable than wt Aβ oligomers [32]. The presence of intracellular Aβ deposits in our mice supports previous observations of intraneuronal Aβ in different tg mice [2, 5, 29], and in post-mortem brain tissue from patients with AD [12, 13]. Together with these observations, our findings support a role of intracellular Aβ in causing functional impairment before the onset of β-amyloid plaque pathology.

Between 9 and 15 months of age, β-amyloid plaques became a prominent feature in our arcAβ mice; these were highly consistent in all tg mice examined. Their characteristic dense of core morphology differed from cotton wool-like structure of plaques seen with the Swe mutation alone. In addition, severe CAA was also present at this age; with dense Aβ aggregates decorating blood vessels walls and spreading from there into the parenchyma. This pathology was much more pronounced as compared to tg mice expressing the Swe mutations alone. The different β-amyloid plaque morphology and the characteristic decoration of blood vessel walls compared to Swe tg mice may be related to distinctly different mechanisms of aggregation caused by the Arc mutations. Other APP mutations close to or at the same position as the Arc mutation are also related with severe CAA [17, 28], and a recent study expressing the Dutch mutation within Aβ, showed that Dutch Aβ is targeted extensively to the vasculature without depositing parenchymal β-amyloid plaques [18]. Together with the observations that clearance of Duch Aβ into the blood was reduced due to lower binding affinities to receptors that mediate the transport across the BBB [9, 30], our results of the double labeling of arcAβ β-amyloid plaques and blood vessels imply that CAA may be a seeding origin of dense cored plaques. Reduced clearance of Arc Aβ could foster its accumulation at outer vessel walls where it leads ultimately to degeneration and disappearance of the initial blood vessel [38]. Similar vascocentric dense-core plaques are also present in AD patients with the Flemish mutation [24].

Our arcAβ mice model the pathophysiological effects of early intraneuronal Aβ deposits in vivo, as well as the vascular clearance failure of Aβ aggregates from brain parenchyma into blood vessels. The finding that intracellular deposits of Aβ can occur early in the natural history of β-amyloid formation, and that they are associated with impaired behavior, underscore their potential role as therapeutic targets for disrupting the amyloid cascasde, and for rescuing related functional impairments.

Example 8

Amyloid Pathology in Aged APP ArcAβ Transgenic Mice and Effects on Chronic Treatment with Human Anti-Aβ Antibody NI-101.10

Animals

ArcAβ mice were generated as described in the previous Examples on a hybrid background of C57Bl/6 and DBA2. The test group was backcrossed once to C57Bl/6. Mice were kept under standard housing conditions on a reversed 12 h:12 h light/dark cycle and had free access to food and water. The treatment groups were balanced for age and gender.

Human Antibodies

Recombinant human anti-Aβ antibody NI-101.10 was produced in stably transfected 293 HEK cells and purified using standard Protein A column purification. Control antibody Humira (Adalimumab, Abbott, Switzerland) was dissolved in medium conditioned by 293 HEK cells and purified as described.

Passive Immunization Treatment 24 month old arcAβ mice were injected weekly i.p. with recombinant human NI-101.10 or Humira control antibody (3 mg/kg body weight) over a time period of 2 months (8 injections). The allocation of mice to the individual groups was: n=5 μg and 4 wt for the NI-101.10 treatment groups; n=5 μg and 6 wt for the control antibody treatment groups.

Immunohistochemistry

Mice were anesthetized (10 ul/g bw ketamin/xylaxine) and perfused transcardially with PBS. One brain hemisphere was dissected into cortex, hippocampus and cerebellum and immediately frozen on dry-ice for further biochemical analysis. The other hemisphere was fixed in 4% paraformaldehyde and embedded in paraffin. 5 μm sagittal sections were cut with a Leica RM 2135 microtome (Bannockburn, Ill.). ThioflavinS staining and Congo Red staining were performed according to standard protocols available at IHC world (www.ihcworld.com). 2-3 sections per mouse brain spaced 75 μm apart were used for each staining. 2 images per section were taken at 10× magnification for cortex analysis (parietal and frontal region). The entire hippocampus area (5× magnification cropped to ROI) was taken for the hippocampus analysis. All stained sections were imaged using an inverted microscope (Leica DMIRE2).

Results

Figure 7:
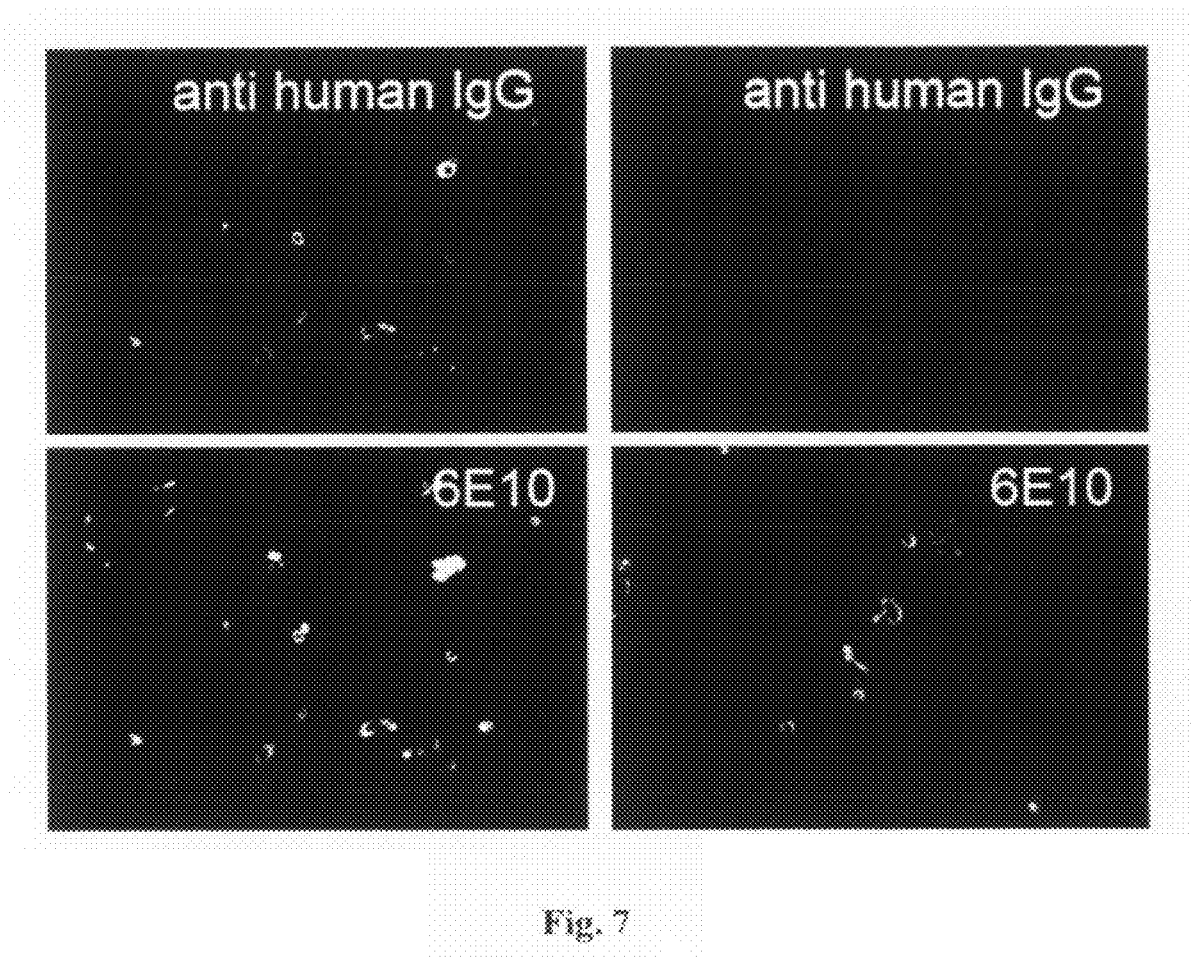
FIG. 7: Blood brain barrier penetration and decoration of amyloid plaques by peripherally administered NI-101.10. NI-101.10 can cross the blood brain barrier and bind to β-amyloid deposits in NI-101.10 treated mice (left panel) whereas no such staining is visible in animals treated with the human control antibody (right panel).

To assess the pharmacological effects of chronic treatment with recombinant NI-101.10, 24 month APPswe/arc mice and their wildtype littermates were injected weekly IP with 3 mg/kg of NI-101.10 for 2 months. Double staining of brain sections from immunized arcAβ mice with 6E10 and anti-human IgG revealed binding of NI-101.10 to Aβ deposits (FIG. 7, left panel), indicating that NI-101.10 can cross the blood brain barrier and bind to brain β-amyloid plaques. No such binding of human antibody to Aβ deposits was seen in control antibody treated arcAβ mice (FIG. 7 right panel).

Figure 8:
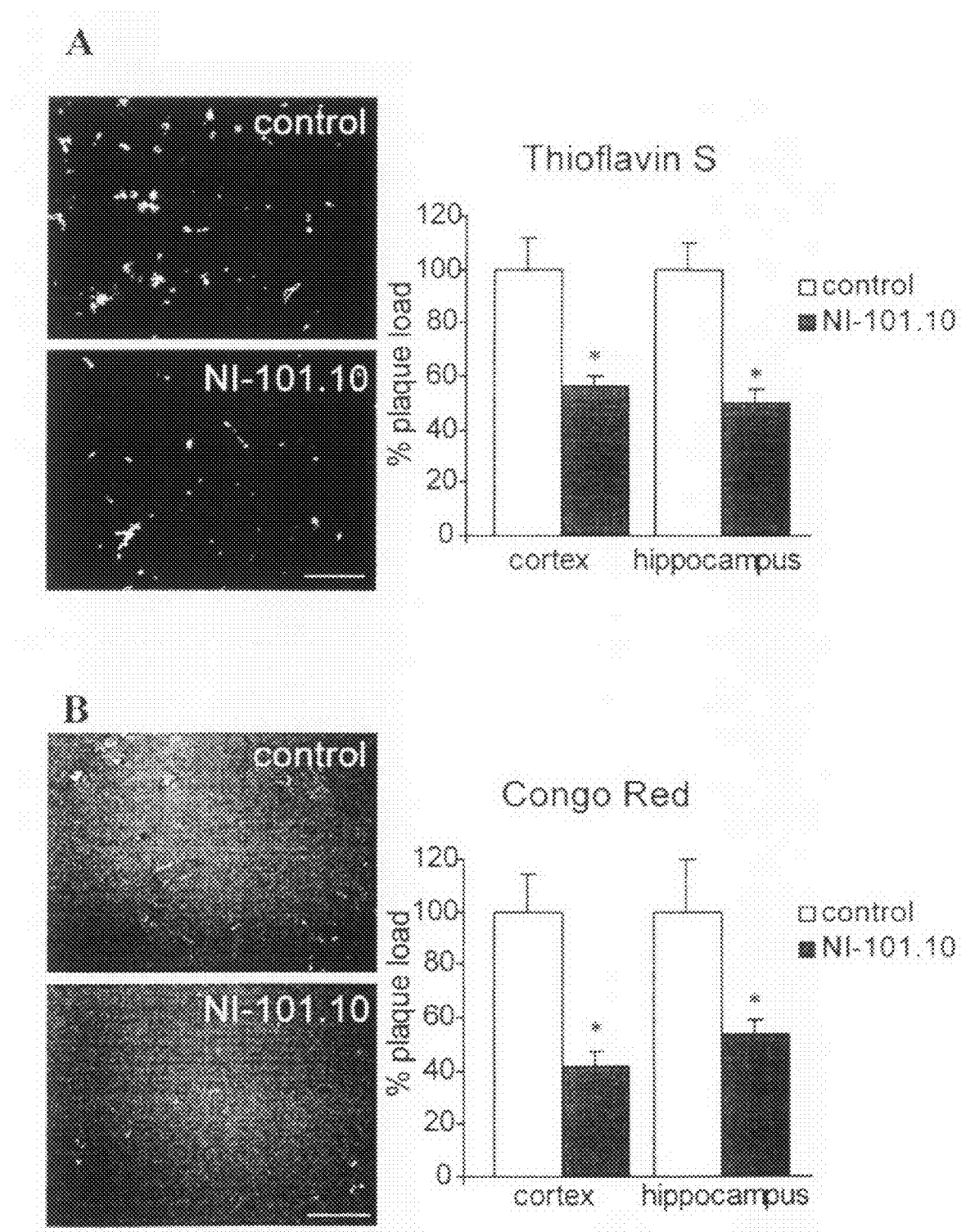
FIG. 8: Passive immunization with NI-101.10 reduces β-amyloid load in APPswe/arc mice. (A, B) Thioflavin S and Congo Red plaque load analyses reveal significant reductions of more than 50% compared to the control antibody treated animals (Mann-Whitney U; p=0.02 for cortex, p=0.009 for hippocampus for ThioS and p=0.009 for cortex and p=0.04 for hippocampus for Congo Red analysis). Scale bar: 200 um. (C-E) Thioflavin S analysis reveals a significant reduction in β-amyloid burden (C), number of β-amyloid plaques (D) and average plaque size (E) in NI-101.10 treated APPswe/arc mice compared to control treated animals. Mann-Whitney U statistics: p=0.02 for plaque area cortex; p=0.009 for plaque area hippocampus; p=0.047 for plaque number cortex; p=0.047 for plaque number hippocampus; p=0.009 for plaque size cortex; p=0.009 for plaque number hippocampus).
Figure 8:
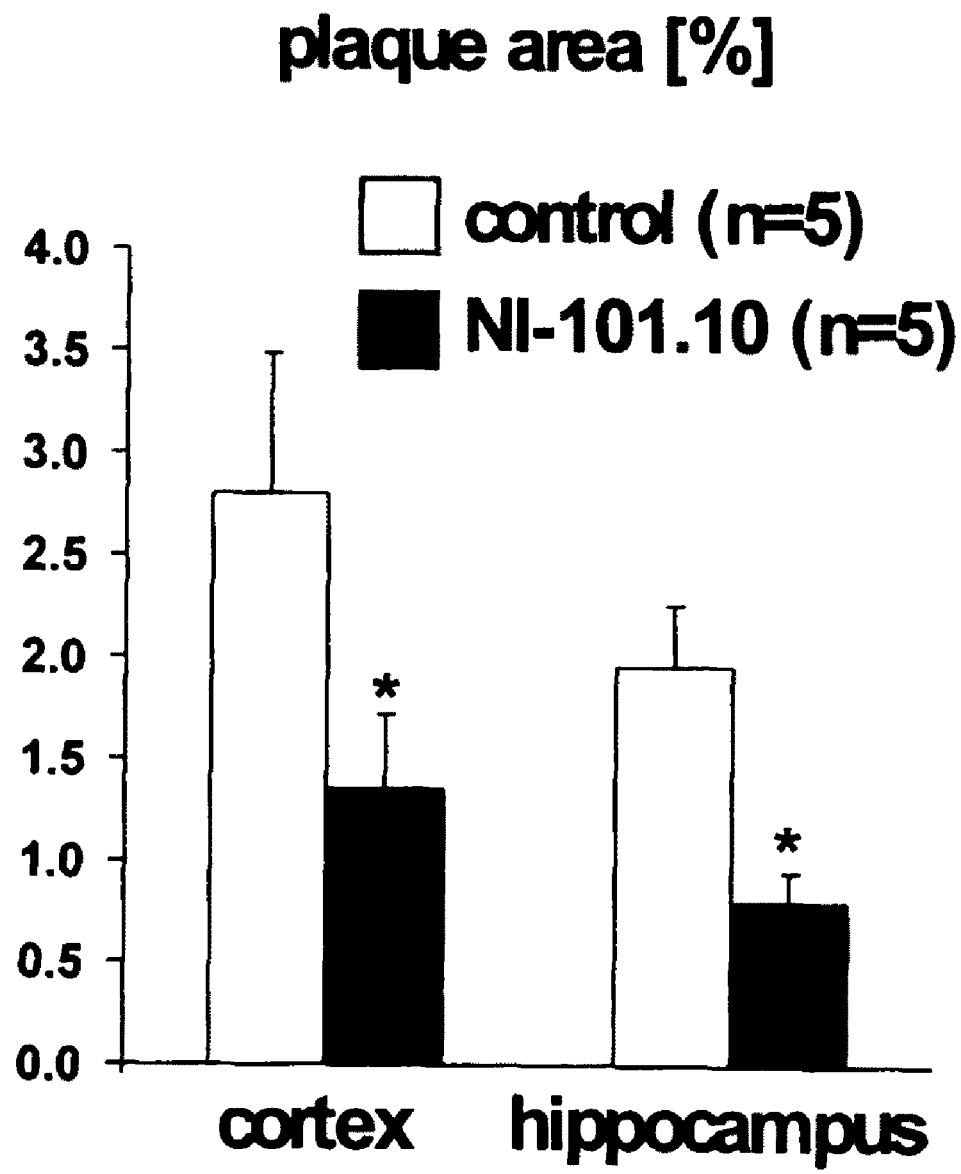
Figure 8:
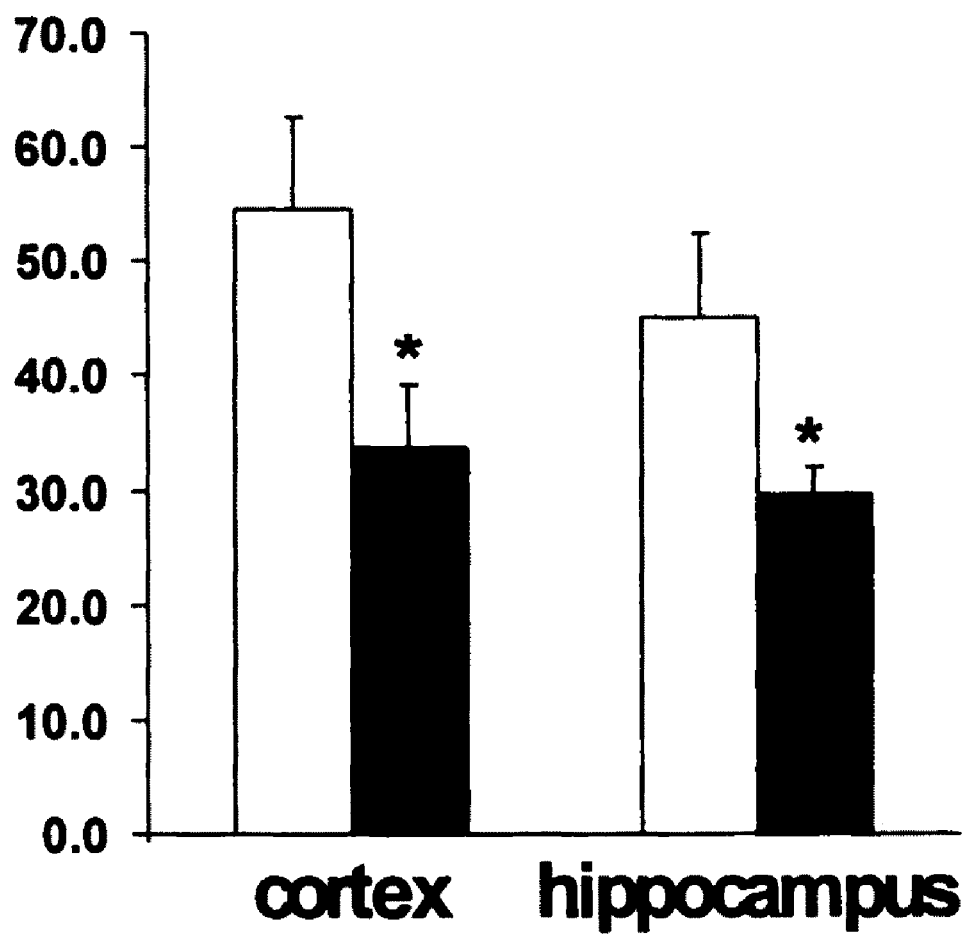
Figure 8:
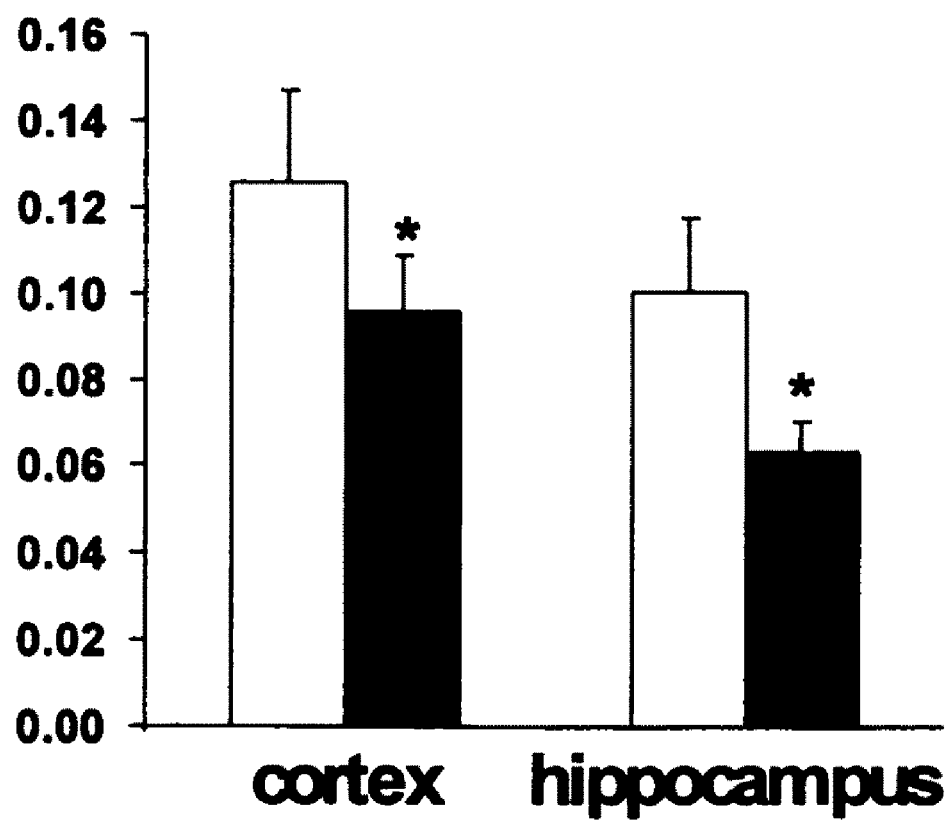

Chronic treatment with 3 mg/kg of NI-101.10 resulted in a significant reduction of amyloid plaque load as was revealed by Thioflavin S and Congo Red staining. This reduction reached levels of greater than 50% in cortex and hippocampus compared to control antibody-treated arcAβ mice (FIGS. 8A, B). In addition to the plaque area (FIG. 8C), significant reductions were also observed for the number of plaques (FIG. 8D) and the average plaque size (FIG. 8E).

In conclusion, the transgenic ArcAβ mice of the present invention displays severe brain β-amyloid plaques substantially resembling those observed in Alzheimer patients. Peripherally administered recombinant NI-101.10 antibody can cross the blood brain barrier and bind to brain β-amyloid plaques. Chronic NI-101.10 treatment results in significant reductions of brain amyloid plaque burden in aged APP transgenic mice.

Example 9

Vascular Reactivity and Brain Blood Flow in Aged APP ArcAβ Transgenic Mice and Effects of Chronic NI-101.10 Treatment Via Passive Immunization Animals, human antibodies and passive immunization treatment as described in Example 8.

fMRI Measurements

ArcAβ mice and their wildtype littermates were measured before (n=3 tg and 3 wt) or after the antibody treatment (n=5 tg NI-101.10, 4 tg Humira, 6 wt NI-101.10, 6 wt Humira). Mice were anesthetized with Isofluran, intubated and artificially ventilated during the MR experiment. The mice were placed on a water-heated cradle and all agents were injected via cannula into the tail vein. Experiments were performed on a 4.7 Tesla Pharmascan 47/16 (Bruker BioSpin GmbH, Germany). Scan parameters of the RARE sequence (Hennig et al., Magn. Reson. Med. 3 (1986), 823-833) were set as followed: spatial resolution: $156 \times 156 \times 700$ μm$^3$, temporal resolution: 40 s, repetition time: 2500 ms, echo time (eff. TE): 80.2 ms, field of view (FOV): $2 \times 1.3$ cm$^2$, RARE factor: 32, matrix dimension: $128 \times 128$, slice thickness: 0.7 mm, interslice distance: 1.2 mm, number of averages: 4, number of slices: 5. fMRI measurement comprised 3 phases: 8 baseline images (S pre) were acquired as reference for the determination of the relative cerebral blood volume ($CBV_{rel}$) changes. Thereafter, scanning was interrupted and contrast agent (Endorem 55 mg/kg) was injected as a bolus. After 15 min to allow for contrast agent to reach steady state concentration, 7 postcontrast images (S(0)) were acquired. Manual injection of acetazolamide was followed by acquisition of 51 images (S(t)). For the stimulation paradigm 30 mg/kg Acetazolamide was used, a carbon anhydrase inhibitor that acts as a global vasodilator and leads to an increase in cerebral blood, volume. Data analysis was carried out using Biomap. Changes of $CBV_{rel}$ in percentage of baseline values ($\Delta CBV_\%$) were computed on a pixel by pixel basis according to $\Delta CBV_\%(t)=(\ln(S(t)/S(O)))/(\ln(S(O)/Spre))*100$.

Results

Figure 9:
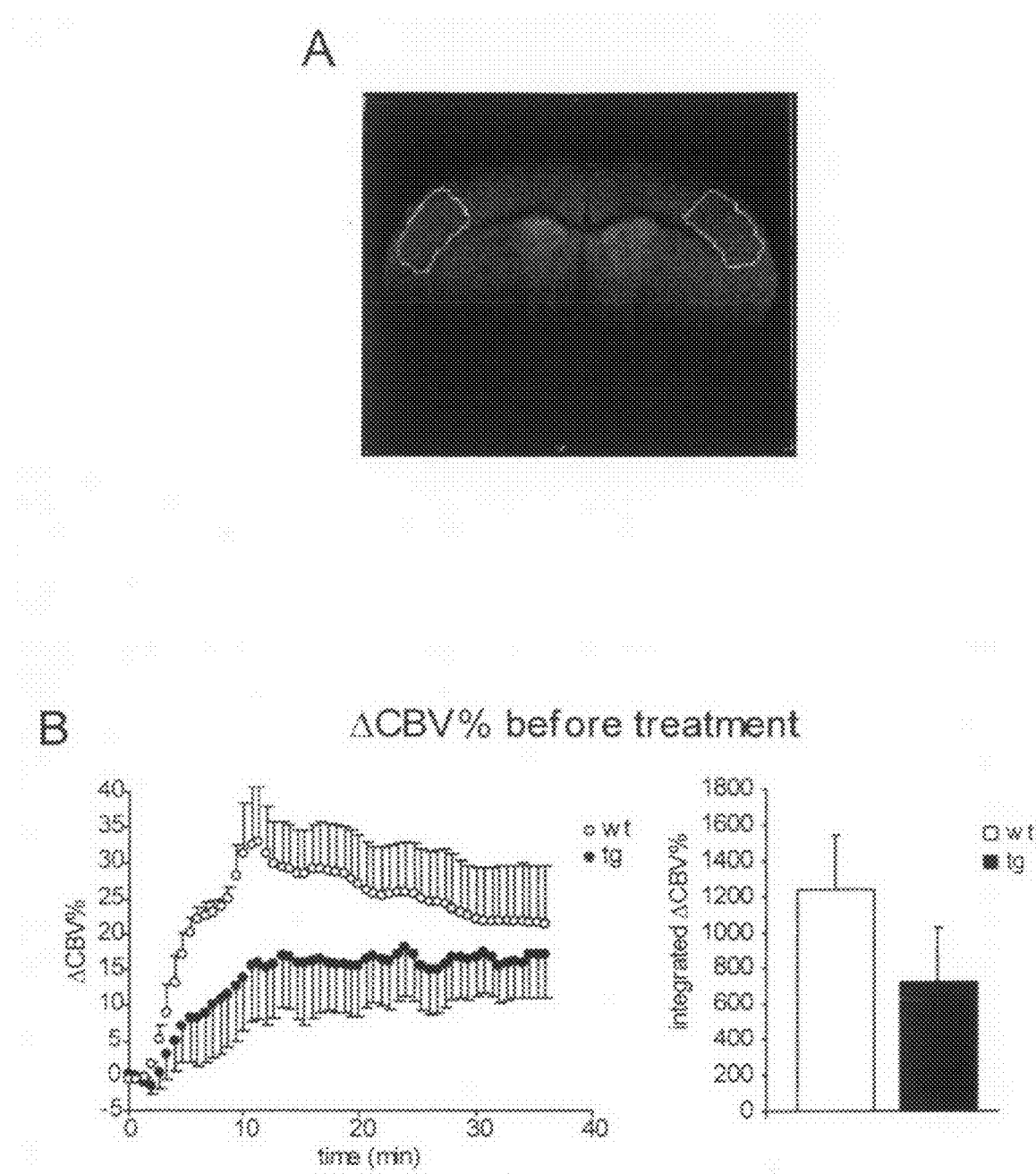
FIG. 9: fMRI reveals improved vasodilative properties in NI-101.10 treated arcAβ mice A) Structural fMRI image with regions of interest. B) Change in cerebral blood volume (ACBV %) after injection of the vasodilator acetazolamide. ArcAβ mice show a reduced vascular response when compared to their wt littermates. C) Treatment with NI-101.10 improves the impaired vasodilative properties of blood vessels in arcAβ mice. NI-101.10 treated mice show 20% larger changes in brain blood flow when compared to the control antibody treated transgenic littermates.
Figure 9:
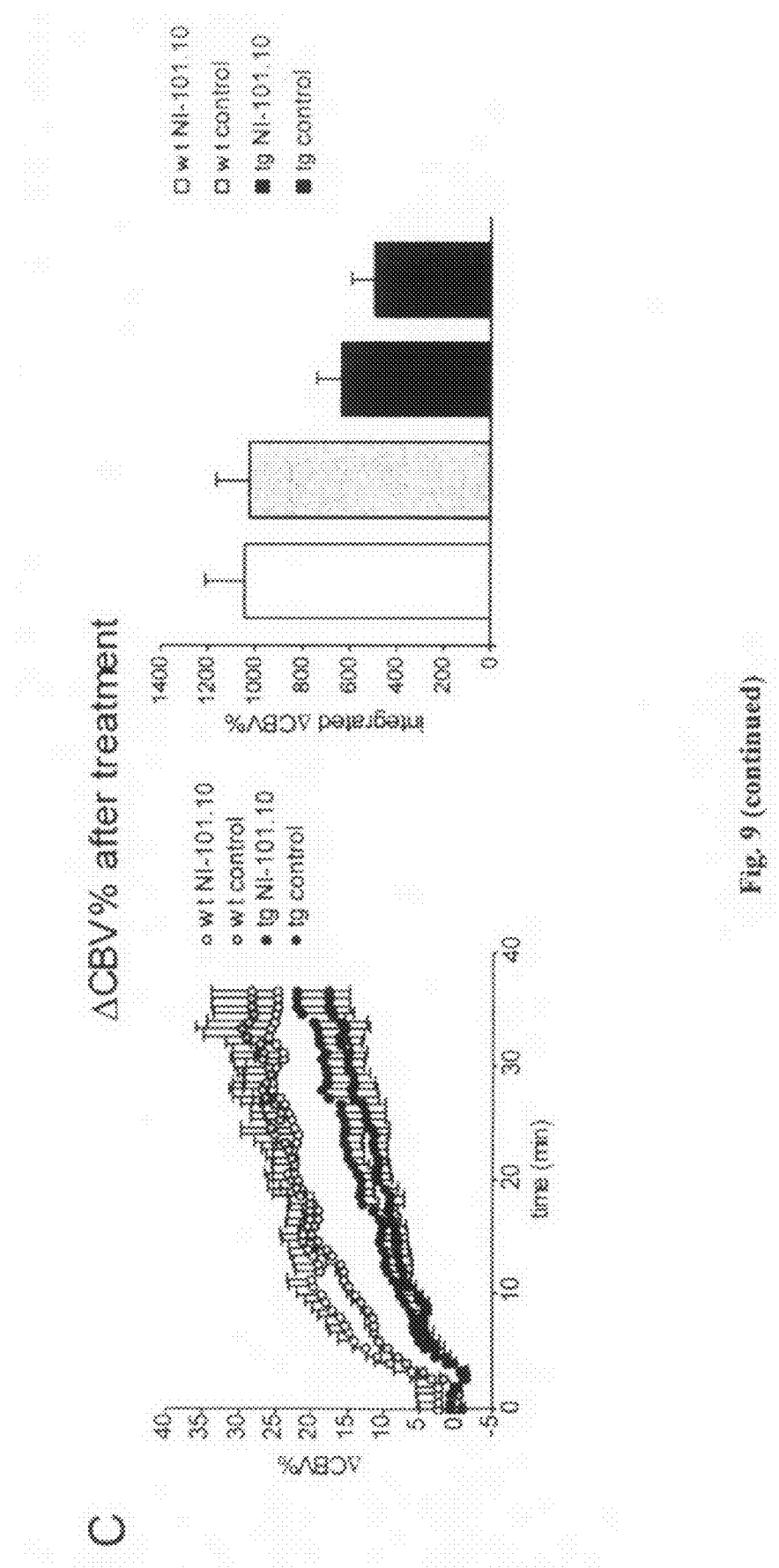

Previous reports suggested an association of cerebral amyloid angiopathy (CAA) with compromised vascular reactivity in a transgenic mouse model with CAA (Mueggler et al., J. Neurosci. 22 (2002), 7218-7224). The severe cerebral amyloid angiopathy (CAA) occurring in old arcAβ mice (see Example 7) might thus constrain the vasodilative flexibility of affected blood vessels. To address whether there is reduced vascular reactivity in arcAβ mice we measured vascular reactivity to a pharmacological vasodilative stimulus (acetazolamide) by functional magnetic resonance imaging (fMRI) in vivo. Acetazolamide is a clinically used carbonic anhydrase inhibitor that increases the cerebral blood flow within minutes after application by raising the concentration of $CO_2$ in the blood (Settakis et al., Eur. J. Neurol. 10 (2003), 609-620). A group of 24 month old arcAβ mice (n=3 μg and 3 wt) was measured using this stimulation paradigm. Whereas wildtype mice showed a rapid increase in cerebral blood volume ($\Delta CBV_\%$) in the parietal cortex, the change in $CBV_\%$ was limited in the arcAβ mice (FIGS. 9A and B). A comparison of the integrated ACBV % over time after the acetazolamide injection revealed an impairment of vascular reactivity in arcAβ mice (FIG. 9B).

To examine the pharmacological effects of chronic NI-101.10 treatment on blood vessel reactivity, 24 month APPswe/arc mice and their wildtype littermates were injected weekly i.p. with 3 mg/kg of NI-101.10 for 2 months. After completion of the treatment regimen, vasodilative properties were measured by fMRI. ArcAβ mice displayed a 30% lower response to acetazolamide when integrated $\Delta CBV_\%$ values were compared (FIG. 9C; Mann-Whitney-U; p=0.002 for tg vs wt). The NI-101.10 treated group of transgenic animals showed an increase in integrated ACBV % of about 20% when cto their control antibody treated transgenic littermates (mean ACBV % NI-101.10 tg=639 vs. mean ACBV % Hum tg=500), indicating improved vasodilative properties after NI-101.10 treatment.

In summary, the transgenic ArcAβ mice of the present invention display impaired vasoreactivity and cerebral blood flow, which can be improved by treatment with an anti-Aβ antibody.

Example 10

Figure 10:
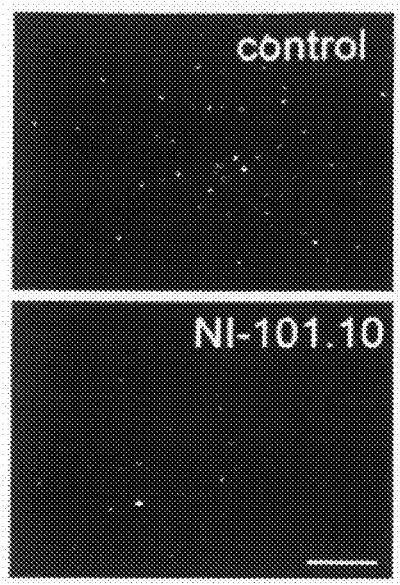
FIG. 10: Reduced β-amyloid load is accompanied by decreased astrocytosis and microgliosis A) Quantification of anti-GFAβ staining revealed a significant reduction in the number of reactive astrocytes in the cortex of NI-101.10 treated arcAβ mice when compared to control treated transgenics. B) Quantification of Iba-1 staining showed a trend towards a reduced number of activated microglia in NI-101.10 treated mice in cortex and hippocampus. Scale bar: 200 µm
Figure 10:
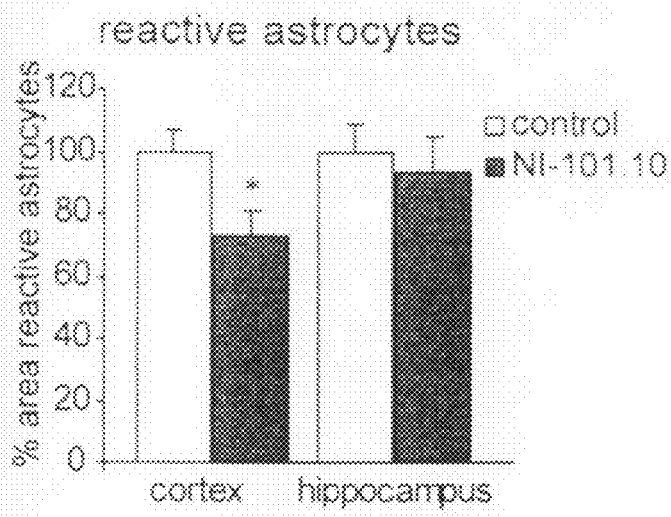
Figure 10:
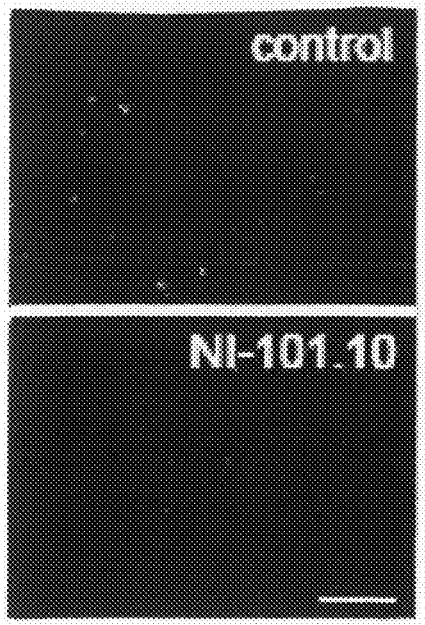
Figure 10:
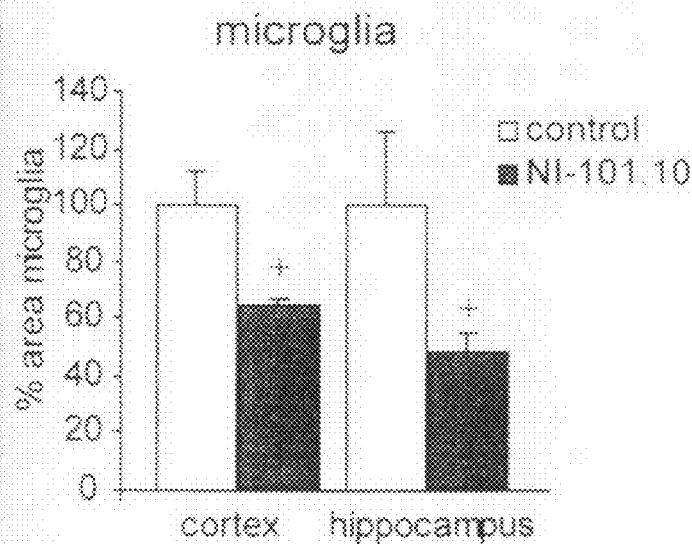

Reactive Astrocytes and Microglia in Aged APP ArcAβ Transgenic Mice and Effects of Chronic NI-101.10 Treatment Animals, human antibodies, and passive immunization treatment as described in Examples 8 and 9.
Immunohistochemistry Mice were anesthetized (10 μl/g bw ketamin/xylaxine) and perfused transcardially with PBS. One brain hemisphere was dissected into cortex, hippocampus and cerebellum and immediately frozen on dry-ice for further biochemical analysis, the other hemisphere was fixed in 4% paraformaldehyde and embedded in paraffin. 5 μm sagittal sections were cut with a Leica RM 2135 microtome (Bannockburn, Ill.). For immunohistochemistry, slices were dewaxed, blocked with 4% BSA, 5% goat serum and 5% horse serum in PBS for 1 h at RT. Antibodies were incubated overnight at 4° C. using the following dilutions: anti GFAP (Advanced Immunochemicals) 1: 500, anti IBA1 (WAKO) 1:500. 2nd fluorophore coupled antibodies were incubated at RT for 2 h. Quantification of reactive astrocytes and microglia was done with the software ImageJ (http://rsb.info.nih.gov/ij/). 3 sections per mouse, ~75 μm apart were used for each staining. 2 images per section were taken at 10× magnification for cortex analysis (parietal and frontal region), the whole hippocampal area (5× magnification cropped to ROI) was taken for the hippocampus analysis. All stained sections were imaged using an inverted fluorescence microscope (Leica DMIRE2).
Results To test whether chronic treatment with NI-101.10 affects the neuroinflammatory response in arcAβ mice; reactive astrocytes and microglia were quantified after immunohistological staining. A reduction in the number of reactive astrocytes (anti GFAβ-staining) in cortex of NI-101.10 treated arcAβ mice compared to control antibody treated animals (FIG. 10A; Mann-Whitney-U; p=0.047). No change was detected in the hippocampus. Staining with an antibody against a marker of microglia and macrophages (anti-Iba1) also revealed a statistical trend towards reduced inflammation (FIG. 10B; Mann-Whitney-U; p=0.075 for both cortex and hippocampus). The decrease in astrocytosis and microgliosis is in line with the reduced β-amyloid load observed after NI-101.10 treatment.

In conclusion, the phenotype of astrocytosis and microgliosis observed in patients suffering from severe stage of Alzheimer's disease can be modeled on aged APP ArcAβ transgenic mice. Furthermore, chronic treatment with an anti-Aβ antibody leads to amelioration of the disease phentotype.

Example 11

Frequency of Brain Microhemorrhages in Aged APP ArcAβ Transgenic Mice and Effects of Chronic NI-101.10 Treatment Animals, human antibodies, and passive immunization treatment as described in Examples 8 and 9.
Histochemistry Mice were anesthetized (10 μl/g bw ketamin/xylaxine) and perfused transcardially with PBS.

Figure 11:
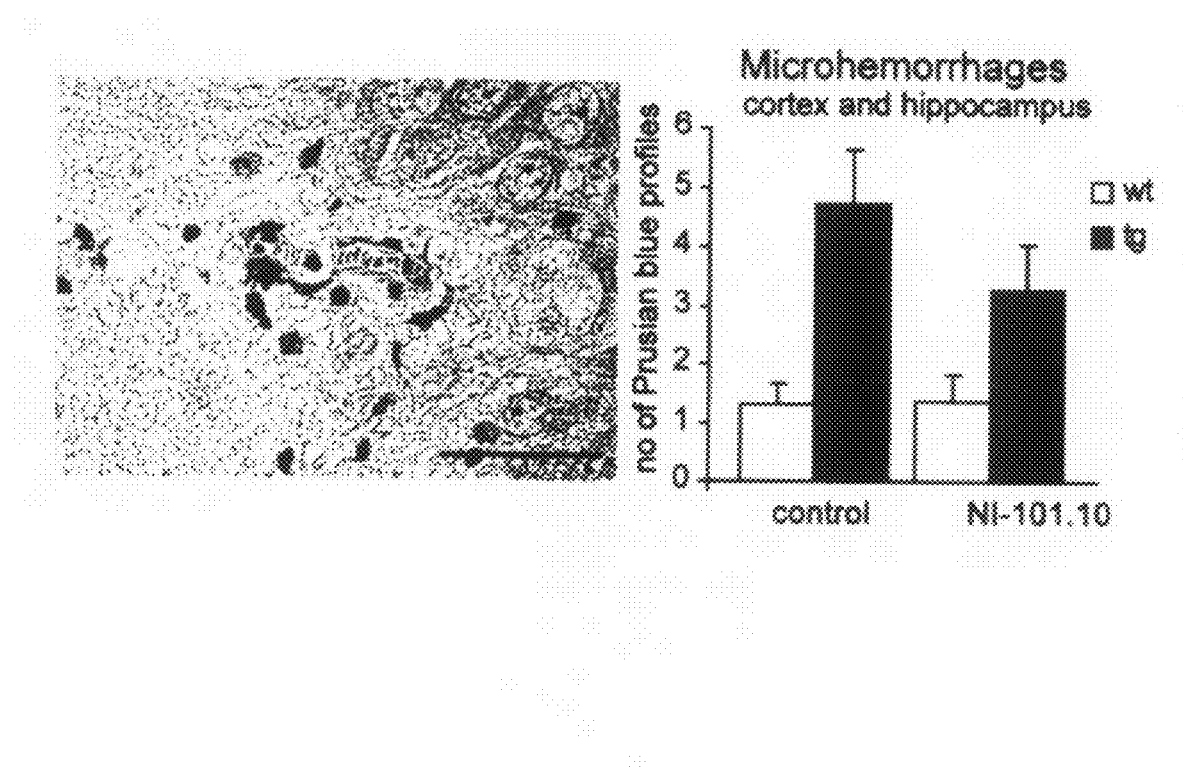
FIG. 11: No change in the number of microhemorrhages upon passive immunotherapy with NI-101.10. Representative picture of a brain microhemorrhage in arcAβ mice revealed by Perl's prussian blue staining (left). Quantitative analysis demonstrates a significantly elevated frequency of micorhemorrhages in arcAβ transgenic mice compared to their wildtype littermates. Chronic treatment with NI-101.10 did not result in increased frequency of micorhemorrhages. Scale bar: 20 µm

One brain hemisphere was dissected into cortex, hippocampus and cerebellum and immediately frozen on dry-ice for further biochemical analysis, the other hemisphere was fixed in 4% paraformaldehyde and embedded in paraffin. 5 μm sagittal sections were cut with a Leica RM 2135 microtome (Bannockburn, Ill.). Perls' Prussian blue stainings were done according to standard protocols available at IHC world (www.ihcworld.com). 2 sections per mouse, ~75 μm apart were used for each staining. 2 images per section were taken at 10× magnification for cortex analysis (parietal and frontal region), the whole hippocampal area (5× magnification cropped to ROI) was taken for the hippocampus analysis. All stained sections were imaged using an inverted fluorescence microscope (Leica DMIRE2).
Results Passive immunotherapy with certain monoclonal antibodies directed against Aβ can be associated with increased frequency of microhemorrhages in the brain (Burbach et al., 2007; Pfeifer et al., 2002; Wilcock et al., 2004) To assess the effects of chronic therapy with NI-101.10, Perl's prussian blue staining was performed on brain sections from arcAβ and wildtype mice after chronic NI-101.10 treatment. This staining reveals the presence of hemosiderin, a breakdown product of haemoglobin, and marker of previous microhemorrages (FIG. 11). In aged arcAβ mice treated with a control antibody, the frequency of Prussian blue positive profiles was significantly elevated compared to wildtype littermates (Mann-Whitney-U; p=0.001). Treatment with the NI-101.10 antibody did not lead to in increase the number of microhemorraghes when compared to control-antibody treated arcAβ mice (Mann-Whitney-U; p=0.347).

In conclusion, it could be established that chronic treatment with NI-101.10 is not associated with increased frequency of brain microhemorrhages in aged ArcAβ transgenic mice.

Example 12

Impaired Working Memory of Aged APP ArcAβ Transgenic Mice and Effects of Chronic NI-101.10 Treatment Animals, human antibodies and passive immunization treatment as described in Examples 8 and 9.
Y-Maze The spontaneous alternation rate was assessed using a Y-shaped plastic maze, with 40×20×10 cm arm sizes. During 5 min sessions, the sequences of arm entries were recorded; alternation was defined as successive entries into the three arms, in overlapping triplet sets. The percent alternation was calculated as the ratio of actual to possible alternations (defined as the total number of arm entries−2) multiplied by 100%. After 2 months of treatment with either NI-101.10 or control antibody, the mice were retested in the Y-maze. The experimenter was blinded for both treatment and genotype during the whole experiment.
Statistical Analysis The Y-maze performance of untreated arcAβ mice and wildtype littermate controls was compared using an unpaired t-test (n=15 wt and 15 tg). The nonparametric Kruskal-Wallis test was used to compare the improvement after treatment in all 4 groups. The nonparametric Mann-Whitney U test was chosen for pair-wise comparison of the different groups. Zero-performers (i.e. mice that did not leave the arm they were placed in) were excluded from the analysis.
Results In order to address the effect of chronic treatment with NI-101.10 on cognitive performance, the animals were tested before and after a two months treatment regimen in the Y-maze, a working memory paradigm. As was observed in previous studies, untreated 24-months old arcAβ mice were significantly impaired compared to their wildtype littermates (FIG. 12A, before treatment; unpaired t-test, p=0.0007).

Figure 12:
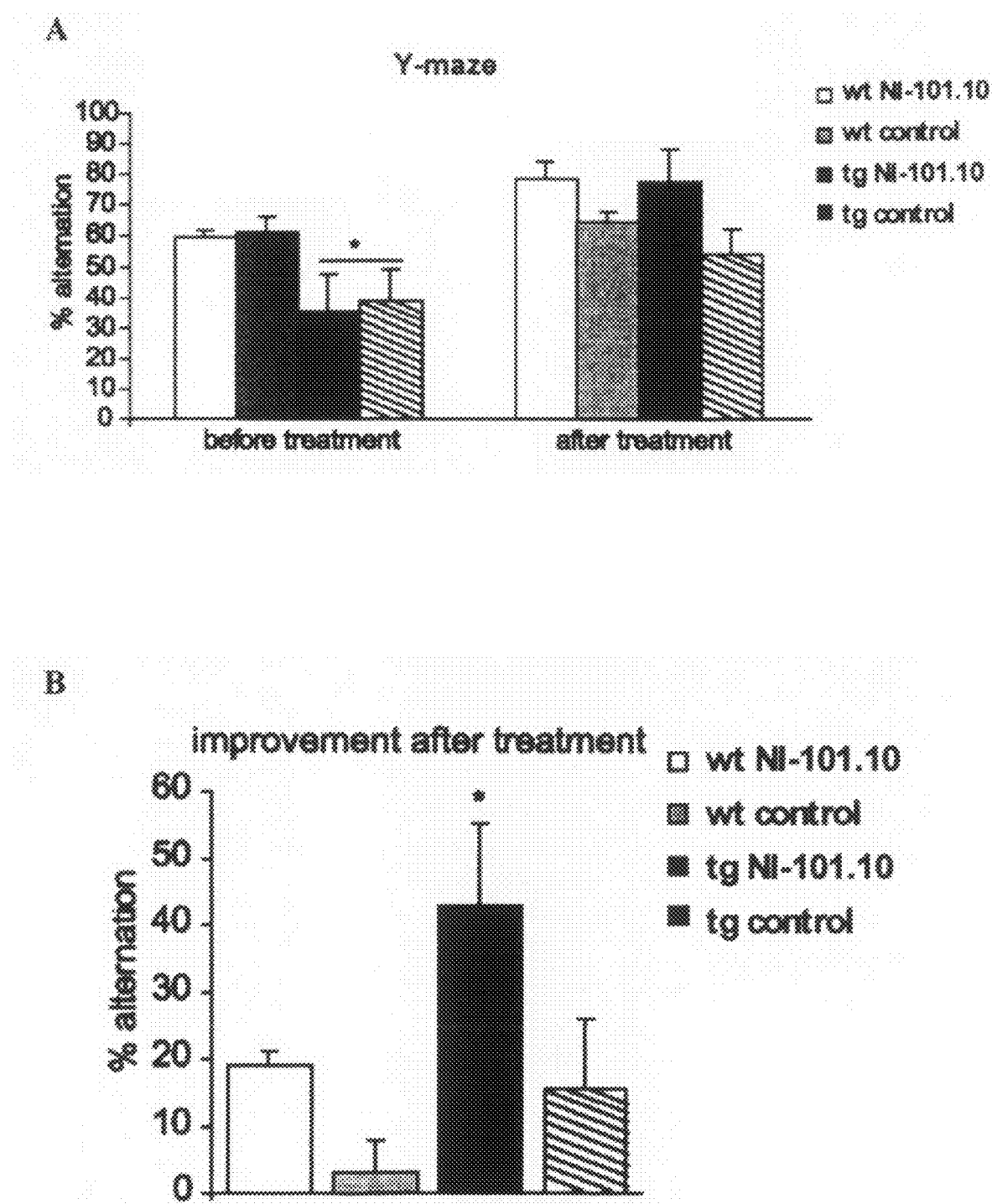
FIG. 12: Improvement of cognitive performance after NI-101.10 treatment in arcAβ mice. A) All mice were tested in the Y-maze at 24 months of age before treatment followed by a re-testing 2 months later upon completion of the treatment. ArcAβ mice were significantly impaired before treatment compared to wt littermates. B) The improvement (performance after treatment minus performance before treatment) did significantly differ between the four groups, with the NI-101.10 treated arcAβ mice showing the largest improvement in performance.

NI-101.10 treated arcAβ mice showed clearly enhanced alteration levels, comparable to NI-101.10 treated wildtype control mice after the 2 months treatment. Analysis of the improvement (i.e. performance after treatment minus performance before treatment) showed a significant difference between the four groups (FIG. 12B, Kruskal-Wallis test; p=0.03). A pair-wise post-hoc analysis between all groups showed that NI-101.10 treated arcAβ mice improved their cognitive performance significantly more than wildtype mice (Mann-Whitney U; p=0.05 NI-101.10 tg vs. NI-101.10 wt; p=0.008 NI-101.10 tg vs. Hum wt). This group of mice also showed a strong trend towards improved performance compared to the control antibody treated transgenic littermates (Mann-Whitney-U; p=0.08 NI-101.10 tg vs. Hum tg). All mice showed a ~10% improvement in performance in the re-testing, which was likely due to the familiar environment of the task.

Accordingly, it could be shown that chronic treatment with NI-101.10 improves memory performance in aged APP transgenic mice.

Example 13

Impaired Memory and Hippocampal Long-Term Potentiation (LTP) in ArcAβ Transgenic Mice can be Reversed As demonstrated in the preceding examples, in the mice of the present invention expression of the mutant APP induces punctate intraneuronal Aβ deposition in several brain areas, and severe behavioral deficits before the onset of extracellular α-amyloid plaque deposition. In this context it could be shown that in these mice, Aβ pathology is associated with an age-dependent impairment in hippocampal LTP in vitro that involves protein phosphatase 1 (PP1)-dependent mechanisms. It could also be demonstrated that both the pharmacologic and genetic inhibition of PP1 in vitro or in vivo abolishes the neurotoxic effect of Aβ-oligomers on synaptic plasticity in arcAβ mice. Thus, the mutant APP transgenic animal of the present invention could be used to identify PP1 a novel potential target for the development of therapeutic approaches designed to block Aβ-mediated toxicity in AD. Accordingly, the potential of the mutant APP transgenic animal of the present invention in screening methods is not limited to Aβ-specific drugs.

Impact of the Present Invention on Research in the Field of Alzheimer's Disease

As demonstrated in the examples, the present invention provides a transgenic animal which models the complex phenotype of Alzheimers disease, i.e. intracellular as well as extracellular parenchymal deposition of Aβ; massive accumulation and deposition of Aβ in cerebral blood vessels; reduced vasoreactivity and brain blood flow; microgliosis and astrocytosis; spontaneous brain micorhemorrhages; cognitive impairments; and hippocampal long-term potentiation (LTP). Moreover, in accordance with the present invention it could be shown that this AD animal model is advantageously suitable for the screening and validation of putative drugs interfering with or compensating the effects due to Aβ accumulation and aggregation, thereby preventing, ameliorating and/or neutralizing the AD phenotype or least some symptoms thereof. Thus, the transgenic non-human animal of the present invention, in particular ArcAβ mouse may advance to be used as a gold standard similar to nude mice in tumor research.

REFERENCES

[1] Arriagada P V, Growdon J H, Hedley-Whyte E T, Hyman B T. Neurofibrillary tangles but not senile plaques parallel duration and severity of Alzheimer's disease. Neurology 1992; 42(3 Pt 1):631-9.

[2] Billings L M, Oddo S, Green K N, McGaugh J L, Laferla F M. Intraneuronal Abeta causes the onset of early Alzheimer's disease-related cognitive deficits in transgenic mice. Neuron 2005; 45(5):675-88.

[3] Borchelt D R, Davis J, Fischer M, Lee M K, Slunt H H, Ratovitsky T, et al. A vector for expressing foreign genes in the brains and hearts of transgenic mice. Genet Anal 1996; 13(6):159-63.

[4] Chapman P F, White G L, Jones M W, Cooper-Blacketer D, Marshall V J, Irizarry M, et al. Impaired synaptic plasticity and learning in aged amyloid precursor protein transgenic mice. Nat Neurosci 1999; 2(3):271-6.

[5] Cheng I H, Palop J J, Esposito L A, Bien-Ly N, Yan F, Mucke L. Aggressive amyloidosis in mice expressing human amyloid peptides with the Arctic mutation. Nat Med 2004; 10(11): 1190-2.

[6] Cleary J P, Walsh D M, Hofmeister J J, Shankar G M, Kuskowski M A, Selkoe D J, et al. Natural oligomers of the amyloidbeta protein specifically disrupt cognitive function. Nat Neurosci 2005; 8(1):79-84.

[7] Crawley J N. Behavioral phenotyping of transgenic and knockout mice: experimental design and evaluation of general health, sensory functions, motor abilities, and specific behavioral tests. Brain Res 1999; 835(1):18-26.

[8] Dahlgren K N, Manelli A M, Stine Jr W B, Baker L K, Krafft G A, LaDu M J. Oligomeric and fibrillar species of amyloidbeta peptides differentially affect neuronal viability. J Biol Chem 2002; 277(35):32046-53.

[9] Deane R, Wu Z, Sagare A, Davis J, Du Yan S, Hamm K, et al. LRP/amyloid beta-peptide interaction mediates differential brain efflux of Abeta isoforms. Neuron 2004; 43(3): 333-44.

[10] Gong Y, Chang L, Viola K L, Lacor P N, Lambert M P, Finch C E, et al. Alzheimer's disease-affected brain: presence of oligomeric A beta ligands (ADDLs) suggests a molecular basis for reversible memory loss. Proc Natl Acad Sci USA 2003; 100(18): 10417-22.

[11] Gotz J, Chen F, van Dorpe J, Nitsch R M. Formation of neurofibrillary tangles in P3011 tau transgenic mice induced by Abeta 42 fibrils. Science 2001; 293(5534): 1491-5.

[12] Gouras G K, Almeida C G, Takahashi R H. Intraneuronal Abeta accumulation and origin of plaques in Alzheimer's disease. Neurobiol Aging 2005.

[13] Gouras G K, Tsai J, Naslund J, Vincent B, Edgar M, Checker F, et al. Intraneuronal Abeta42 accumulation in human brain. Am J Pathol 2000; 156(1):15-20.

[14] Haass C, Steiner H. Protofibrils, the unifying toxic molecule of neurodegenerative disorders? Nat Neurosci 2001; 4(9):859-60.

[15] Hardy J A, Higgins G A. Alzheimer's disease: the amyloid cascade hypothesis. Science 1992; 256(5054): 184-5.

[16] Harper J D, Wong S S, Lieber C M, Lansbury Jr P T. Assembly of A beta amyloid protofibrils: an in vitro model for a possible early event in Alzheimer's disease. Biochemistry 1999; 38(28):8972-80.

[17] Hendriks L, van Duijn C M, Cras P, Cruts M, Van Hul W, van Harskamp F, et al. Presenile dementia and cerebral haemorrhage linked to a mutation at codon 692 of the beta-amyloid precursor protein gene. Nat Genet. 1992; 1(3):218-21.

[18] Herzig M C, Winkler D T, Burgermeister P, Pfeifer M, Kohler E, Schmidt S D, et al. Abeta is targeted to the vasculature in a mouse model of hereditary cerebral hemorrhage with amyloidosis. Nat Neurosci 2004; 7(9):954-60.

[19] Hock C, Konietzko U, Streffer J R, Tracy J, Signorell A, Muller-Tillmanns B, et al. Antibodies against beta-amyloid slow cognitive decline in Alzheimer's disease. Neuron 2003; 38(4):547-54.

[20] Holcomb L A, Gordon M N, Jantzen P, Hsiao K, Duff K, Morgan D. Behavioral changes in transgenic mice expressing both amyloid precursor protein and presenilin-1 mutations: lack of association with amyloid deposits. Behav Genet. 1999; 29(3):177-85.

[21] Hsiao K, Chapman P, Nilsen S, Eckman C, Harigaya Y, Younkin S, et al. Correlative memory deficits, Abeta elevation, and amyloid plaques in transgenic mice. Science 1996; 274(5284):99-102.

[22] Hyman B T, Marzloff K, Arriagada PV. The lack of accumulation of senile plaques or amyloid burden in Alzheimer's disease suggests a dynamic balance between amyloid deposition and resolution. J Neuropathol Exp Neurol 1993; 52(6):594-600.

[23] Kamino K, Orr H T, Payami H, Wijsman E M, Alonso M E, Pulst S M, et al. Linkage and mutational analysis of familial Alzheimer disease kindreds for the APP gene region. Am J Hum Genet. 1992; 51(5):998-1014.

[24] Kumar-Singh S, Cras P, Wang R, Kros J M, van Swieten J, Lubke U, et al. Dense-core senile plaques in the Flemish variant of Alzheimer's disease are vasocentric. Am J Pathol 2002; 161(2):507-20

[25] Lambert M P, Barlow A K, Chromy B A, Edwards C, Freed R, Liosatos M, et al. Diffusible, nonfibrillar ligands derived from Abeta1-42 are potent central nervous system neurotoxins. Proc Natl Acad Sci USA 1998; 95(11):6448-53.

[26] Lashuel H A, Hartley D M, Petre B M, Wall J S, Simon M N, Walz T, et al. Mixtures of wild-type and a pathogenic (E22G) form of Abeta40 in vitro accumulate protofibrils, including amyloid pores. J Mol Biol 2003; 332(4):795-808.

[27] Lesne S, Koh M T, Kotilinek L, Kayed R, Glabe C G, Yang A, et al. A specific amyloid-beta protein assembly in the brain impairs memory. Nature 2006; 440(7082):352-7.

[28] Levy E, Carman M D, Fernandez-Madrid I J, Power M D, Lieberburg I, van Duinen S G, et al. Mutation of the Alzheimer's disease amyloid gene in hereditary cerebral hemorrhage, Dutch type. Science 1990; 248(4959): 1124-6.

[29] Lord A, Kalimo H, Eckman C, Zhang X Q, Lannfelt L, Nilsson L N. The Arctic Alzheimer mutation facilitates early intraneuronal Abeta aggregation and senile plaque formation in transgenic mice. Neurobiol Aging 2006; 27(1):67-77.

[30] Monro O R, Mackic J B, Yamada S, Segal M B, Ghiso J, Maurer C, et al. Substitution at codon 22 reduces clearance of Alzheimer's amyloid-beta peptide from the cerebrospinal fluid and prevents its transport from the central nervous system into blood. Neurobiol Aging 2002; 23(3):405-12.

[31] Mullan M, Crawford F, Axelman K, Houlden H, Lilius L, Winblad B, et al. A pathogenic mutation for probable Alzheimer's disease in the APP gene at the N-terminus of beta-amyloid. Nat Genet. 1992; 1(5):345-7.

[32] Nilsberth C, Westlind-Danielsson A, Eckman C B, Condron M M, Axelman K, Forsell C, et al. The 'Arctic' APP mutation (E693G) causes Alzheimer's disease by enhanced Abeta protofibril formation. Nat Neurosci 2001; 4(9):887-93.

[33] Richardson J C, Kendal C E, Anderson R, Priest F, Gower E, Soden P, et al. Ultrastructural and behavioural changes precede amyloid deposition in a transgenic model of Alzheimer's disease. Neuroscience 2003; 122(1):213-28.

[34] Selkoe D J. Alzheimer's disease: genotypes, phenotypes, and treatments. Science 1997; 275(5300):630-1.

[35] Walsh D M, Klyubin I, Fadeeva J V, Cullen W K, Anwyl R, Wolfe M S, et al. Naturally secreted oligomers of amyloid beta protein potently inhibit hippocampal long-term potentiation in vivo. Nature 2002; 416(6880):535-9.

[36] Wirths O, Multhaup G, Bayer T A. A modified beta-amyloid hypothesis: intraneuronal accumulation of the beta-amyloid peptide—the first step of a fatal cascade. J Neurochem 2004; 91(3):513-20.

[37] Wolfer D P, Litvin O, Morf S, Nitsch R M, Lipp H P, Wurbel H. Laboratory animal welfare: cage enrichment and mouse behaviour. Nature 2004; 432(7019):821-2.

[38] Zlokovic B V. Neurovascular mechanisms of Alzheimer's neurodegeneration. Trends Neurosci 2005; 28(4): 202-8.

The invention claimed is:

1. A transgenic mouse whose genome comprises a transgene, said transgene comprising a DNA sequence encoding a human amyloid precursor protein (hAPP) comprising Alzheimer's disease (AD) pathogenic mutations; wherein said DNA sequence is operably linked to the prion protein (PrP) promoter; wherein said hAPP is human APP 695 (hAPP 695), wherein the mutations are the Arctic mutation E693G and the Swedish mutations K670N, M671L; and further wherein said transgene is expressed and results in the deposition of amyloid-β (Aβ) in the brain parenchyma and cerebral blood vessels and is associated with reduced vasoreactivity and brain blood flow.

2. The transgenic mouse of claim 1, wherein the endogenous APP is expressed.

3. The transgenic mouse of claim 1, which displays extensive cerebral amyloid angiopathy and/or spontaneous brain microhemorrhages.

* * * * *